(12) United States Patent  
Miyazaki

(10) Patent No.: US 7,254,437 B2  
(45) Date of Patent: Aug. 7, 2007

(54) MR IMAGING PROVIDING TISSUE/BLOOD CONTRAST IMAGE

(75) Inventor: Mitsue Miyazaki, Otawara (JP)

(73) Assignee: Kabushiki Kaisha Toshiba, Kanagawa-Ken (JP)

( * ) Notice: Subject to any disclaimer, the term of this patent is extended or adjusted under 35 U.S.C. 154(b) by 0 days.

(21) Appl. No.: 10/635,685

(22) Filed: Aug. 7, 2003

(65) Prior Publication Data

US 2004/0059213 A1    Mar. 25, 2004

Related U.S. Application Data

(62) Division of application No. 09/293,062, filed on Apr. 16, 1999, now abandoned.

(30) Foreign Application Priority Data

Apr. 17, 1998  (JP) ................................ 10-108256  
Mar. 2, 1999   (JP) .................................. 11-54614

(51) Int. Cl.  
   *A61B 5/055*    (2006.01)

(52) U.S. Cl. ....................... 600/410; 324/307; 324/309

(58) Field of Classification Search ................ 600/410; 324/307, 309  
See application file for complete search history.

(56) References Cited

U.S. PATENT DOCUMENTS 5,335,660 A * 8/1994 Dumoulin ................... 600/419  
2002/0169372 A1  11/2002 Miyazaki

* cited by examiner

*Primary Examiner*—Ruth S. Smith  
(74) *Attorney, Agent, or Firm*—Nixon & Vanderhye P.C.

(57) ABSTRACT

A magnetic resonance imaging (MRI) system includes an ECG detector for the patient object being imaged and an element for performing an MRI pulse sequence. An imaging unit defined by the pulse sequence is longer in temporal length than one heart beat represented by the EGG signal. An MR signal is acquired from the object in response to the pulse sequence and an MR image based on the acquired MR signal is produced. A plurality of divided MT pulses can be applied instead of the conventional single MT pulse. In this case, an SE-system pulse sequence having a shorter echo train spacing is used, to generate sounds by applying gradient pulses incorporated in an imaging pulse sequence so as to automatically instruct a patient to perform an intermittent breath hold during three-dimensional scanning.

16 Claims, 21 Drawing Sheets

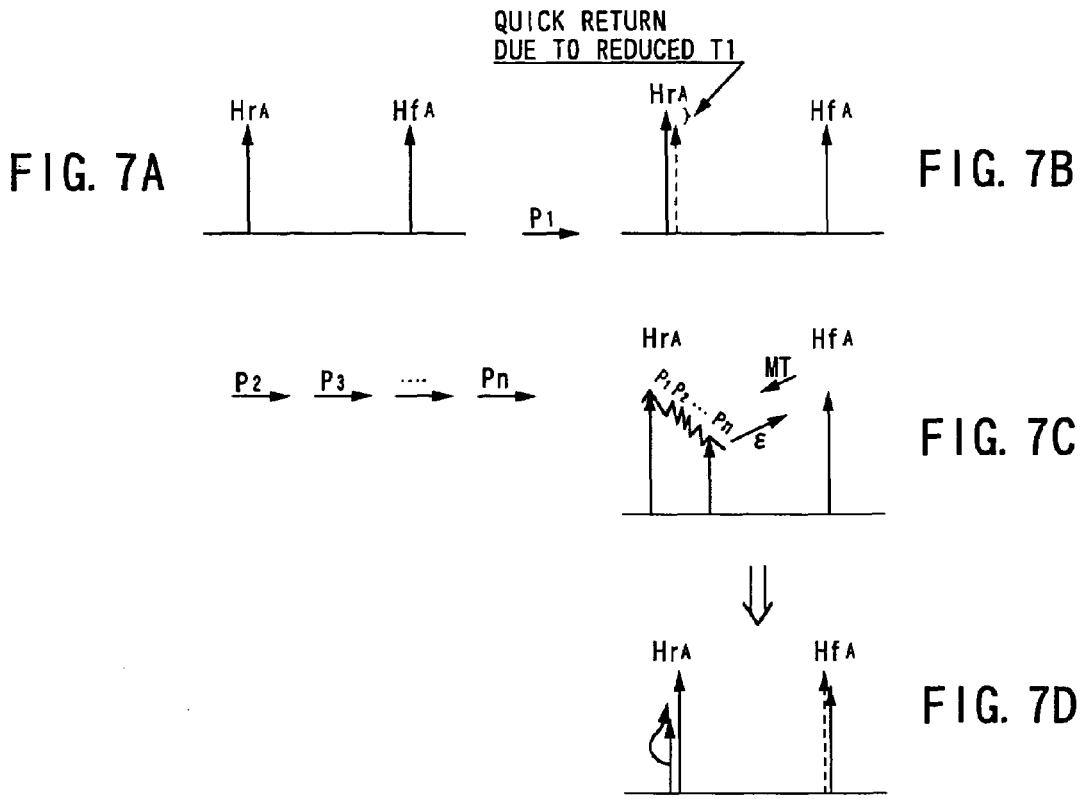
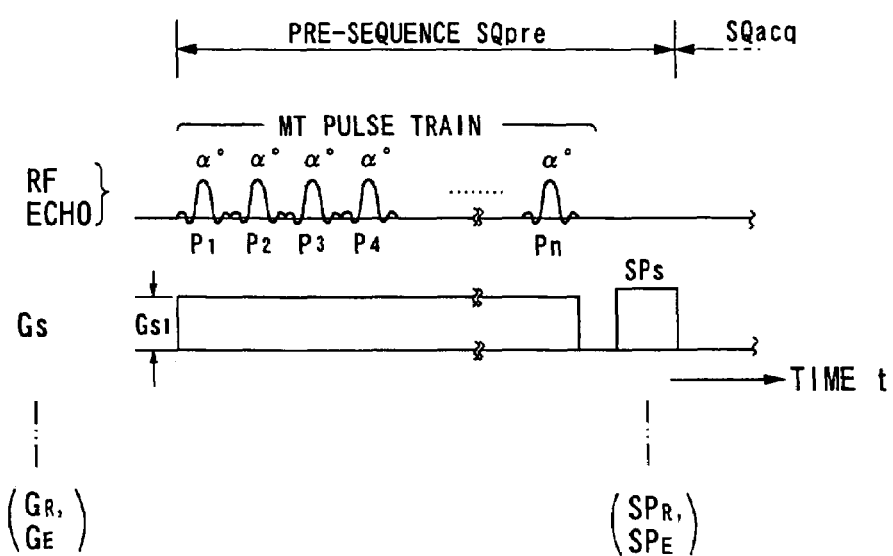

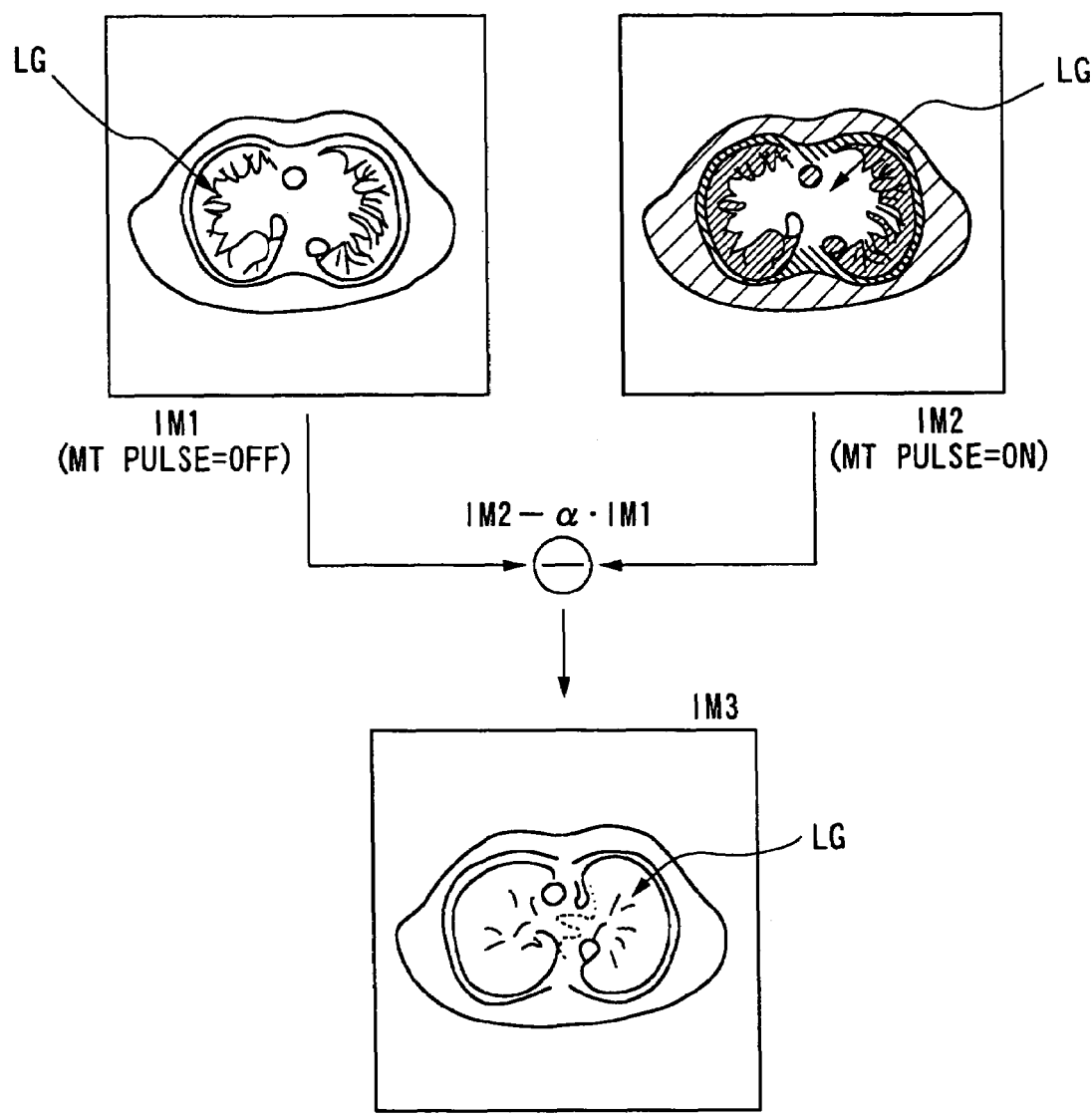

MR IMAGING PROVIDING TISSUE/BLOOD CONTRAST IMAGE

RELATED APPLICATION

This is a divisional of our application Ser No. 09/293,062 filed Apr. 16, 1999 now abandoned.

BACKGROUND OF THE INVENTION

1. Field of the Invention

The present invention relates to magnetic resonance imaging for imaging blood vessels and tissue of a subject (patient) on the basis of a magnetic resonance phenomenon occurring in the subject. More particularly, this invention is concerned with a magnetic resonance imaging (MRI) system and magnetic resonance (MR) imaging method that provides tissue/blood contrast images of a higher quality.

In one aspect, such images are provided by utilizing MT (magnetization transfer) pulses that are able to greatly raise contrast between blood (or flow of blood) and tissue. In another aspect, such high-quality tissue/blood contrast images are obtained by acquiring a plurality of echo signals responding to one exciting pulse incorporated in a pulse sequence to which both a degree of resolution and a time for echo acquisition are optimized. In this later case, a patient's breath hold is improved by using an easier self-navigation technique.

2. Description of the Related Art

Magnetic resonance imaging (MRI) is a technique for magnetically exciting nuclear spins of a subject positioned in a static magnetic field by applying a radio-frequency (RF) signal with the Larmor frequency, and reconstructing an image using MR signals induced by the excitation.

One field of magnetic resonance (MR) imaging is MR angiography. A phase contrast method is one technique for MR angiography, which uses pulses referred to as flow encoding pulses. Another method for MR angiography is to utilize MT effects (or what may be referred to as MTC (magnetization transfer contrast effects) to produce images to produce contrast between blood (flow of blood) and tissue. Recently this technique has frequently been used. One such example is disclosed by U.S. Pat. No. 5,050,609 (Magnetization Transfer Contrast and Proton Relaxation and Use thereof in Magnetic Resonance Imaging).

The research of MT effects originates from the study of a ST (saturation transfer) method by Forsen & Hoffman (refer to "Forsen et al., Journal of Chemical Physics, Vol.39(11), pp.2892-2901 (1963)"). The MT effects are based on chemical exchanges and/or cross relaxation between protons of a plurality of types of nuclear pools, such as free water and macromolecules.

Several conventional MR angiography techniques that use MT effects are discussed below.

In each of FIGS. 1A to 1C, the left-side graph represents the frequency spectra of free water and macromolecules, while the right-side one illustrates the exchange and relaxation relation of their magnetizations Mr and Mf. As shown in the spectra of protons of free water and macromolecules, the free water of which T2 (spin-spin) relaxation time is longer (T2 is approx. 100 msec) and the macromolecules of which T2 relaxation time is shorter (T2 is approx. 0.1 to 0.2 msec) resonate in the same frequency range. Since the T2 relaxation time of a free water signal is longer, its Fourier-transformed signal has a peak with a relatively narrow half-width, as shown. However, in the case of the signal of protons whose movement is restricted among macromolecules, such as protein, its Fourier-transformed signal exhibits a relatively broader half-width value, due to a shorter T2 relaxation time, no longer appearing as a distinct peak in the spectra.

When taking the resonance peak frequency $f_o$ of free water as the center frequency, a frequency-selective pulse serving as an MT pulse is applied to excite a frequency range shifted, for example, by 500 Hz from the center frequency $f_o$ of free water (that is, off-resonance excitation), as shown in the left side of FIG. 1B. This excitation causes the magnetization Hf of free water and those Hr of macromolecules, both of which are in equilibrium as shown in the right side of FIG. 1A, to change relative to one another as the magnetization Hf of free water moves to the Hr of macromolecules as shown in the right side of FIG. 1B. As a result of it, as illustrated in the left-side graph of FIG. 1C, the signal value of protons of free water decreases. Differences in signal values are caused between one region in which the chemical exchanges and/or cross relaxation between free water and macromolecules are reflected and the other region in which such chemical exchanges and/or cross relaxation is not reflected. These differences lead to differences in contrast between flow of blood and tissue, providing blood flow images.

At present, MR angiography based on MT effects is classified into spatially non-selective imaging and slice-selective imaging.

As an example of the former, "G. P. Pike, MRM 25, 327-379, 1992" describes a frequency-selective binomial pulse used as the MT pulse and applied in a spatially non-selective manner. Contrast between parenchyma and flow of blood is obtained according to a relation of "MT effects of parenchyma >MT effects of flow of blood."

As an example of the latter imaging, a proposal by "M. Miyazaki, MRM 32, 52-59, 1994." This paper teaches that a slice-selective MT pulse uses an RF excitation pulse having an application time that is relatively long and accompanied by gradient spoiler pulses. Application of such an MT pulse causes MR signals to be emanated from stationary parenchyma in a slice to be imaged to be lowered more than in a flow of blood that passes therethrough, due to its MT effects. MT effects received by flow of blood that comes into the slice also cause a signal decease (but, the degree of signal decrease from flow of blood is less than that from parenchyma). This provides contrast between flow of blood and parenchyma.

However, in the case of the foregoing MR angiography making use of a slice-selective MT pulse, blood flowing into a slice to be imaged suffers from a considerably large amount of MT effects, because a flip angle given to magnetization when the MT pulse is applied is set to a greater amount (for example, 500 to 1000 degrees). This results in MR signals manated from the blood passing the slice to significantly decrease in magnitude. Therefore, contrast between blood and parenchyma is not always fully satisfied under recent needs for higher image resolution.

In addition, in the field of MRI, another clinically significant imaging technique is T2-weighted imaging that emphasizes the T2 relaxation phenomenon.

To perform this imaging requires that the repetition time TR be longer. The entire scanning takes as long as 10 minutes, for example, imposing a greater burden on a patient. To improve this, FSE (Fast Spin Echo) and EPI (Echo Planar Imaging) methods are proposed that produce a plurality of echo signals in response to one excitation pulse.

The EPI method is used to switch a readout gradient between the two polarities to produce field echoes consecutively. This enables single-shot imaging.

The FSE method is characteristic of using a plurality of refocus pulses that are applied after the application of one excitation (shot) pulse and produce multiple echoes. Compared to the EPI method, the FSE method needs a loner scanning (imaging) time, but posses various advantages, such as higher resistance to the non-uniformity of a static magnetic field. Therefore, the FSE method of which number of shots are increased and effective TE (Echo Time) is shortened have been widely used for providing a clinical effectiveness.

On one hand, for depicting cardiac vascular systems, synchronization with the cardiac temporal phase, which is typically represented by an ECG signal, is unavoidable. In addition, field-echo-system pulse sequences whose repetition time TR and/or echo time TE are shortened are used for reduced scanning time in imaging cardiac vascular systems. Particularly, a segmented FFE (Fast FE) can raise a temporal efficiency for scanning, which has been used widely. In the FFE sequences, if the TR or TE is reduced, image contrast is lowered. Thus, to compensate for this lowered contrast, an MT pulse and/or fat-suppression pulse are preferably used. In addition, when considering the fact that three-dimensional imaging takes a long time for scanning, it is, in fact, impossible to force a patient to continue her or his breath hold for such a long scanning time. A continuous imaging is therefore executed in synchronism with an ECG signal. In this ECG-gating imaging, a problem arises in that the heart moves with its respiration. One solution to respiratory motions is selection or correction of data using a navigator echo produced by a navigation pulse incorporated in an imaging pulse sequence.

In general, in cases it is desired to quickly obtain T1-weighted images or PD (proton density)-weighted images, FE-system pulse sequences are superior to others. On the contrary, if T2-weighted images whose sensitivity for lesions is excellent, pulse sequences that are capable of acquiring a plurality of echo signals in response to one excitation time are effective, increasing efficiency in data acquisition. Particularly, for T2-weighted images whose TR or TE is elongated, the EPI or FSE method is preferable and allows total scanning time to be reduced and image artifacts to be suppressed.

However, on account of the fact that conventional T2-weighted images obtained with the EPI or FSE method is based on a multi-slice technique, a signal from blood inflowing into a certain slice to be imaged has already been saturated by the RF excitation for other slices. Hence this T2-weighted imaging provides blood signals of less intensities, being inappropriate for the depiction of flow of blood.

A report has been made that imaging T2-weighted images three-dimensionally makes it possible to depict a vascular system utilizing the characteristic that a region where blood flows slowly is longer in the T2 relaxation time than a parenchyma region. However, even when using this reported technique, images of a sufficient contrast between blood and tissue are still unavailable, independently of the magnitudes of flow of blood. In this three-dimensional imaging, when the number of slices excited per unit time are reduced, there is a tendency that it becomes difficult to reduce signals from muscle or the liver, the signal reduction resulting from MT effects according to the FSE method. Thus the contrast between such tissue and blood is lowered.

As described above, 3D imaging with a continuous breath hold is normally difficult or impossible. In the conventional 3D MR imaging or 3D MR angiography for the abdomen, an intermittent breath hold may have been carried out to reduce artifacts due to respiratory body motions. A respiration-gating technique may have been used for achieving timing to a patient's respiration.

However, since there is no steady way of informing a patient of the timing of the respiration, this respiration gating has not been popularly used in normal clinical fields. An operator needs to instruct a patient to hold the breath at imaging sites each time of the intermittent breath holds. Thus, operative burdens to the operator will be increased. There is a large possibility that respiration timing fails and image quality becomes poor.

SUMMARY OF THE INVENTION

The present invention attempts to break through the foregoing current situations.

An object of the present invention to largely increase contrast between blood and parenchyma compared to the prior method by decreasing the influence of MT effects given blood, so that a higher depiction blood flow image or parenchyma image is gained in imaging by which a distinction is made by MT pulses between blood in motion and stationary blood and/or parenchyma.

Another object of the present invention is to provide T2-weighted images that have tissue contrasts as high as obtained by FE-system pulse sequences or more as well as have less artifacts, thereby being clinically effective.

More practically, the object is to T2-weighted cardiac vessel images that have tissue contrasts between blood and cardiac muscle and/or cardiac wall as high as obtained by FE-system pulse sequences or more as well as have less artifacts.

Still another object of the present invention is to control tissue contrasts by controlling both preventing signals from being lowered and MT effects gained.

Still another object of the present invention is to reduce artifacts due to an ECG-gating technique by employing a breath-hold technique together with the ECG gating.

Still another object of the present invention is to steadily inform a patient of the start timing of an intermittent breath hold, thereby providing images from which artifacts resulting from the patient's respiratory body motions are largely eliminated.

For accomplishing the above objects, a first configuration according to the present invention is provided by A magnetic resonance imaging (MRI) system providing an MR image of an object to be imaged, comprising: means for detecting a signal indicative of cardiac temporal phases of the object; means for performing a pulse sequence toward the object, a unit of imaging defined by the pulse sequence being longer in temporal length than one heart beat represented by the detected signal; means for acquiring an MR signal from the object in response to performance of the pulse sequence; and means for producing the MR image based on the acquired MR signal.

According to a second configuration of the present invention, there is provided a magnetic resonance imaging (MRI) system providing an MR image of a region to be imaged of an object, comprising: means for applying an MT (magnetization transfer) pulse of which frequency is different than a frequency specifying the region to be imaged; means for applying a gradient spoiler pulse after the MT pulse applied;

means for scanning the region to be imaged with a pulse sequence to cause an MR signal from the region; and means for producing the MR image using the MR signal.

Preferably, the MT pulse applied by the MT pulse applying means consists of a plurality of divided MT pulses. It is also preferable that the plurality of divided MT pulses applied by the MT pulse applying means is composed of a plurality of RF (radio frequency) pulses applied slice-non-selectively.

It is further preferred that each of the plurality of divided MT pulses applied by the MT pulse applying means is an RF pulse exciting spins residing in a slice region determined by a frequency thereof, and the system comprises means for applying a gradient pulse, applied concurrently with the RF pulse, for selecting the slice region. In this case, each RF pulse has a shorter applied duration and is given a smaller flip angle for exciting spins of the slice region. It is preferred that the gradient spoiler pulse applying means apply the gradient spoiler pulse in at least one of slice, readout, and phase-encoding directions spatially set toward the object.

According to a third configuration of the present invention, there is provided a magnetic resonance imaging method of providing an MR (magnetic resonance) image of a region to be imaged of an object; the method comprising the steps of: applying an MT (magnetization transfer) pulse of which frequency is different than a frequency specifying the region to be imaged; applying a gradient spoiler pulse after the MT pulse applied; scanning the region to be imaged with a pulse sequence to cause an MR signal from the region; and producing the MR image using the MR signal.

According to a fourth configuration of the present invention, there is provided a magnetic resonance imaging method of acquiring from an object an MR (magnetic resonance) signal based on a magnetic resonance phenomenon of at least two kinds of nuclear pools coupled with each other by at least one of a chemical exchange phenomenon or a cross relaxation phenomenon in the object, comprising the steps of: applying in turn a plurality of divided MT pulses to a region selected in the object, thereby decoupling the coupling of the at least two kinds of nuclear pools; applying a gradient spoiler pulse to the decoupled nuclear pools; and scanning, with a pulse sequence, another region to be imaged different in position from the MT pulse applied region as well as acquiring the MR signal from the another region.

Thus, a plurality of divided MT pulse each of which has a short duration and is assigned to a small flip angle are applied to a region different from another region to be image, and the imaging region is excited in an off-resonance state. The divided MT pulses reduce the apparent T1 relaxation time of blood that is flowing. The spins of blood that is flowing are T1-relaxed at faster speeds and quickly returned to their steady states.

In other words, MT effects given free water of flow of blood are lowered, the total MT effects become small. Compared to the conventional MT pulse, signals from blood that has inflowed into the imaging region are higher. On the other hand, because the parenchyma of the imaging region is stationary or can be regarded as being stationary, the divided MT pulses simply give the parenchyma the sum of MT effects that correspond to the MT pulses. This amount of the MT effects reduced largely as expected.

In consequence, in comparison with the conventional one, the contrast between the blood and parenchyma in an MRA image of this imaging region is improved by an amount that corresponds to the apparently reduced T1 relaxation time against flowing blood, resulting an excellent depiction ability.

According to a fifth configuration of the present invention, there is provided a magnetic resonance imaging (MRI) system providing an MR image of a region to be imaged of an object, comprising: means for performing a pulse sequence including a pre-sequence for applying an MT (magnetization transfer) pulse causing MT effects in spins of the object and an SE(spin echo)-system data acquisition sequence, which follows the pre-sequence, for generating a plurality of echo signals in response to one time of excitation of the spins using an RF (radio frequency) magnetic field; means for acquiring the plurality of echo signals; and means for producing the MR image based on the acquired echo signals.

Preferably, the pulse sequence is applied to either one of a three-dimensional volume region or a two-dimensional slab and formed to perform at least one time of excitation within a repetition time of imaging.

Still preferably, the system further comprises means for detecting a signal indicative of cardiac temporal phases of the object; means for synchronizing start of the pulse sequence with a reference wave of the detected signal; and means for instructing the object to perform an intermittent breath hold according to the detected signal. For example, the detecting means detect an ECG (electrocardiogram) signal of the object as the signal indicative of cardiac temporal phases thereof. It is preferred that the breath-hold instructing means include a gradient pulse incorporated into the pulse sequence, the gradient pulse generating a sound in a gantry of the MRI system when applied.

A sixth configuration of the present invention is that a magnetic resonance (MR) imaging method of providing an MR image of an object, comprising the steps of: performing a pulse sequence including a pre-sequence for applying an MT (magnetization transfer) pulse causing MT effects in spins of the object and an SE(spin echo)-system data acquisition sequence, which follows the pre-sequence, for generating a plurality of echo signals in response to one time of excitation of the spins using an RF (radio frequency) magnetic field; and producing the MR image from the plurality of echo signals.

By the above single-shot imaging, artifacts due to motions in the phase-encoding direction can be suppressed steadily. In addition, artifacts occurring in the slice-encoding direction can be reduced by employing in combination both the ECG gating and intermittent breath hold techniques. It is therefore possible to provide a three-dimensional image having higher value of resolution. When an T2-weighted image of a higher resolution value is obtainable, signals from the cardiac muscle and others can be suppressed by the MT pulse and signals from fat can also be suppressed by the fat-suppression pulse. This enables tissue contrasts between blood and the cardiac muscle and/or cardiac wall to raised greatly. Hence an effective imaging technique for the heart is available.

A seventh configuration of the present invention is that a magnetic resonance imaging system comprising: means for detecting an ECG (electrocardiogram) signal from the object; means for performing a pulse sequence to acquire MR data with an object, including means for synchronizing start of the pulse sequence according to the ECG signal; means for instructing the object an intermittent breath hold according to the ECG signal; and means for producing an MR (magnetic resonance) image through acquiring MR data generated in response to the pulse sequence performed, wherein the breath-hold instructing means include a gradient pulse incorporated into the pulse sequence, the gradient pulse generating a sound in a gantry of the MRI system when applied.

The remaining features of the invention will be clearly understood from the description of various preferred embodiments, which are described with accompanying drawings below.

BRIEF DESCRIPTION OF THE DRAWINGS

In the accompanying drawings:

FIGS. 7A to 7D illustrate MT effects on divided MT pulses against spins of free water and macromolecules of an object in motion;

FIG. 8 is part of a pulse sequence showing another example of applying divided MT pulses;

FIGS. 16A to 16C illustrate a weighted difference process carried out as one image-processing step;

DESCRIPTION OF THE PREFERRED EMBODIMENTS

First Embodiment

A first embodiment of the present invention will now be described FIGS. 2 to 7.

Figure 2:
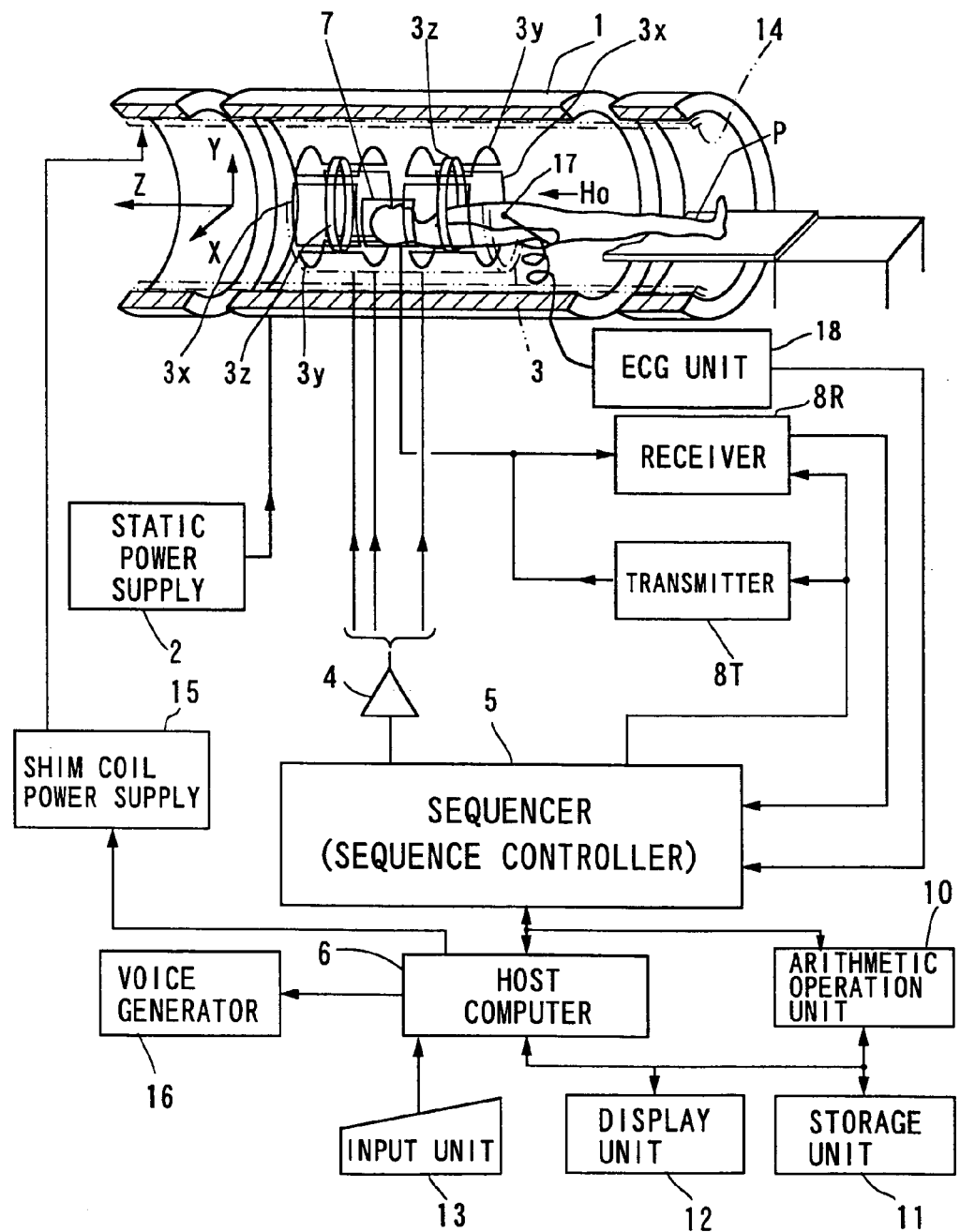
FIG. 2 exemplifies in a block form an MRI system used in various embodiments of the present invention.

FIG. 2 shows the outlined configuration of a magnetic resonance imaging (MRI) system in accordance with the embodiment of the present invention, which will be described below.

The MRI system comprises a patient couch on which a patient P lies down, static magnetic field generating components for generating a static magnetic field, magnetic field gradient generating components for appending positional information to a static magnetic field, transmitting/receiving components for transmitting and receiving a radio-frequency (RF) signal, control and arithmetic operation components responsible for control of the whole system and for image reconstruction, electrocardiographing components for acquiring an ECG signal of a patient, which is a representative of signals indicative of cardiac temporal phases of the patient, and breath hold instructing components for instructing the patient to perform a breath hold.

The static magnetic field generating components includes a magnet 1 that is of, for example, a superconducting type, and a static power supply 2 for supplying a current to the magnet 1, and generates a static magnetic field $H_o$ in an axial direction (Z-axis direction) in a cylindrical bore (diagnostic space) into which the patient P is inserted. The magnet unit includes shim coils 14. A current used to homogenize a static magnetic field is supplied from a shim coil power supply 15 to the shim coils 14 under the control of a host computer to be described later. The couch top of the patient couch on which the patient P lies down can be inserted into the bore of the magnet 1 so that the couch top can be withdrawn.

The magnetic field gradient generating components includes a gradient coil unit 3 incorporated in the magnet 1. The gradient coil unit 3 includes three pairs (kinds) of x-, y-, and z-coils $3x$ to $3z$ used to generate magnetic field gradients changing in strength in X-axis, Y-axis, and Z-axis directions that are mutually orthogonal. The magnetic field gradient generator further includes a gradient power supply 4 for supplying a current to the x-, y-, and z-coils $3x$ to $3z$.

The gradient power supply 4 supplies a pulsating current used to generate a magnetic field gradient to the x-, y-, and z-coils $3x$ to $3z$ under the control of a sequencer that will be described later.

The pulsating current supplied from the gradient power supply 4 to the x-, y-, and z-coils $3x$ to $3z$ is controlled, whereby magnetic field gradients changing in the three axial directions, that is, the X-, Y-, and Z-directions are synthesized. Thus, directions in which a slice magnetic field gradient $G_S$, a phase-encoding magnetic field gradient $G_E$, and a readout (frequency-encoding) magnetic field gradient $G_R$ are applied can be specified and changed arbitrarily. The magnetic field gradients to be applied in a slice direction, a phase-encoding direction that is a direction the distribution of spins in which is phase-encoded, and a readout direction that is a direction in which an MR signal is read are superposed on the static magnetic field $H_0$.

The transmitting/receiving components includes a radio-frequency (RF) coil 7 located in the vicinity of a patient P in the scanning space inside the magnet 1, and a transmitter 8T and a receiver 8R connected to the coil 7. Under the control of a sequencer described later, the transmitter 8T supplies RF current pulses with the Larmor frequency, which are used to excite spins to cause nuclear magnetic resonance (NMR), while the receiver 8R receives echo signals (RF signals) via the RF coil 7, and carries out various kinds of signal processing with the echo signals so as to produce a corresponding digital echo data.

Furthermore, the control and arithmetic operation components includes a sequencer 5 (often referred to as sequence controller), a host computer 6, an arithmetic operation unit 10, a storage unit 11, a display unit 12, and an input unit 13.

Among them, the host computer 6, which has a CPU and memories, has the function of providing the sequencer 5 information about a pulse sequence and managing the operations of the entire system, according to installed software programs. The host computer 6 also serves as an element for instructing a patient to perform a breath hold by a voice massage produced using an automatic voice synthesis technique or others.

The sequencer 5, which has a CPU and memories, stores pulse-sequence information sent from the host computer 6, controls a series of operations performed by the gradient power supply 4, transmitter 8T, and receiver 8R according to the stored information, and temporarily receives digital data corresponding to MR signals outputted from the receiver 8R so as to transmit them to the arithmetic operation unit 10.

The pulse-sequence information includes all information required for operating the gradient power supply 4, transmitter 8T, and receiver 8R according to a pulse sequence. Such information includes the strength, duration, and application timing of pulsed currents applied to the x-, y-, and z-coil 3x to 3z.

As the pulse sequence, a two-dimensional (2D) scan or a three-dimensional (3D) scan can be adopted. Available pulse trains are an SE (spin echo) train, FE (field gradient echo) train, FSE (Fast SE) train, FASE (Fast asymmetric SE) train, and others.

In this MRI system, prior to a data acquisition sequence (may referred to as a main sequence), a pre-sequence including RF pulses functioning as MT pulses and gradient spoiler pulses applied to any one or more logic-axis directions (slice, phase-encoding, and readout directions) is applied by the sequencer 5 under the control of the host computer 6.

Figure 3:
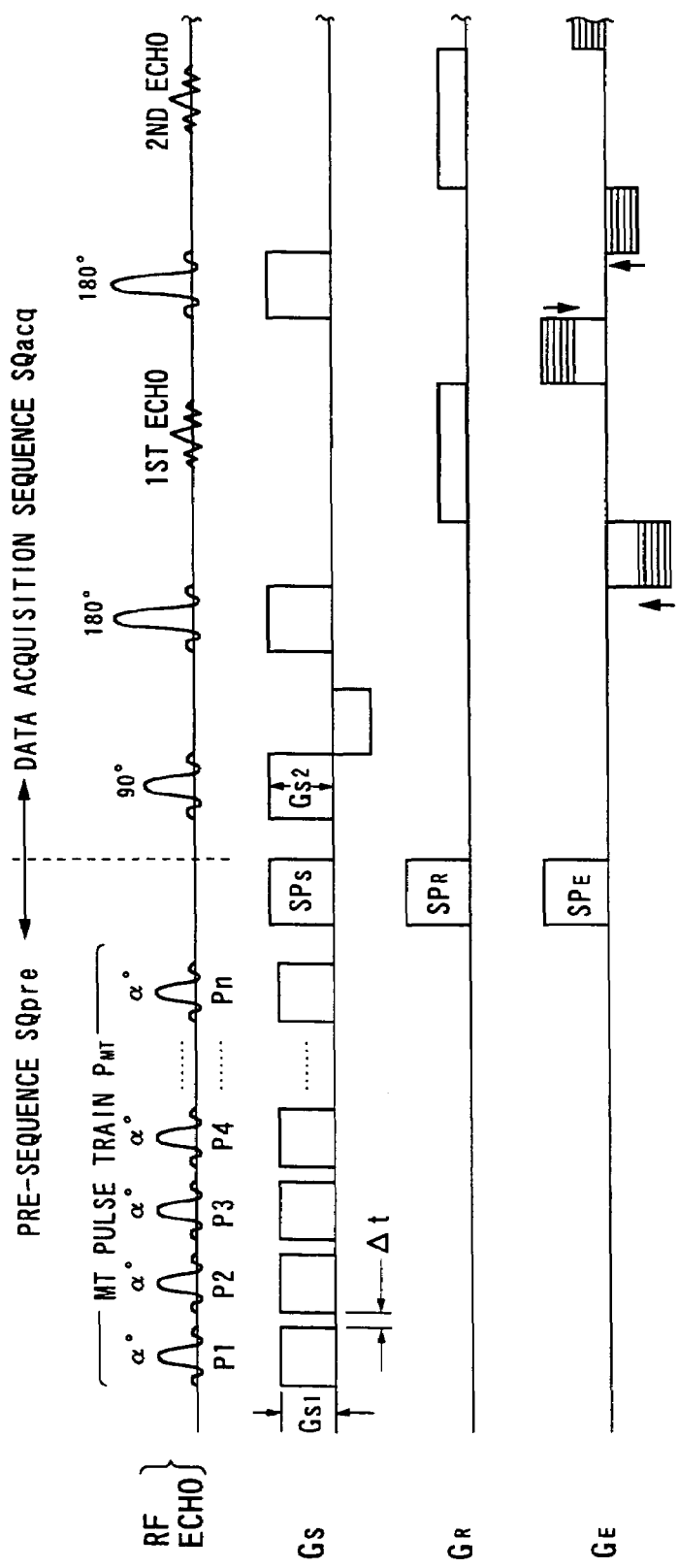
FIG. 3 is a timing chart showing one example of pulse sequences used in a first embodiment.

The MT pulses are set to be applied slice-selectively. In other words, as shown in FIG. 3, the MT pulses are made up of a plurality of RF pulses for excitation which are individually formed by a sinc function, for example, and each RF pulse (i.e., each MT pulse) is accompanied by a slice gradient $G_S$ concurrently applied with it. The number of MT pulses applied is n-pieces (n is an integer larger than 1; for example, ten pieces). The flip angle of each RF (MT) pulse is less than that (larger flip angle, such as 500 to 1000 degrees) of the conventional MT pulse, being a smaller divided value (for example, 90 to 100 degrees). The MT pulses are formed by modulating with a sinc function RF pulses each having a desired frequency offset. Applying those MT pulses will allow parenchyma and free water in a region to be imaged to suffer MT effects. Thus, as in one aspect, a signal from the parenchyma decreases largely than that of free water, producing a larger contrast ratio between them.

The n-sets of the MT pulses and the slice gradients $G_s$ is in turn applied, before a gradient spoiler pulse is applied for dephasing spins of the slice, phase-encoding, and readout directions at a time.

The arithmetic operation unit 10 receives digital echo data sent from the receiver 8R via the sequencer 5, maps the data in a Fourier space (or the k-space or frequency space) formed in an incorporated memory, and performs a two-dimensional or three-dimensional Fourier transform with the mapped data so as to reconstruct an image in the real space. Moreover, the arithmetic operation unit 10 carries out the synthesis of reconstructed image data. The Fourier transform may be performed by the host computer 6, not by the sequencer 5.

The storage unit 11 can preserve raw echo data and reconstructed image data. The display unit 12 displays an image, and can be used to input to the host computer 6 desired information entered into the input unit 13 by an operator; such as, information about parameters for determining an ECG-gating time, scan conditions, the type of pulse sequence, and the type of technique of image synthesis.

The voice generator 16, which composes a constituent of the breath-hold instructing components, utters, for example, a voice message informing a patient of the start or end of breath hold in response to commands sent from the host computer 6. However, this generator 16 may be removed unless the breath-hold instruction is carried out or if it is carried out by any other means.

Furthermore, the electrocardiographing components comprises an ECG sensor 17 attached to the patient body to detect an electric ECG signal and an ECG unit 18 performing various processes including digitization with the detected ECG signal and sending it to both the host computer 6 and the sequencer 5. This measured ECG signal is used by the host computer 6 and the sequencer 5 to perform an ECG-gating scan. The operation of the MRI system according to this embodiment will be described with reference to FIGS. 3 to 7.

First, a pulse sequence for MR angiography shown in FIG. 3 is executed in response to a command from the sequencer 5.

As shown therein, the pulse sequence is composed of a pre-sequence $SQ_{pre}$ previously executed before each RF excitation and a data acquisition sequence $SQ_{acq}$ that follows the previous one.

The pre-sequence $SQ_{pre}$ includes a train of MT pulses $P_{MT}$ causing MT effects and a set of gradient spoiler pulses $SP_S$, $SP_R$, and $SP_E$. The train of MT pulses $P_{MT}$ consists of a plurality of exciting RF pulses $P_1, P_2, P_3, \ldots, P_n$ applied in turn as MT pulses and a plurality of slice gradients $G_S$ applied in parallel with those MT pulses.

Figure 4A:
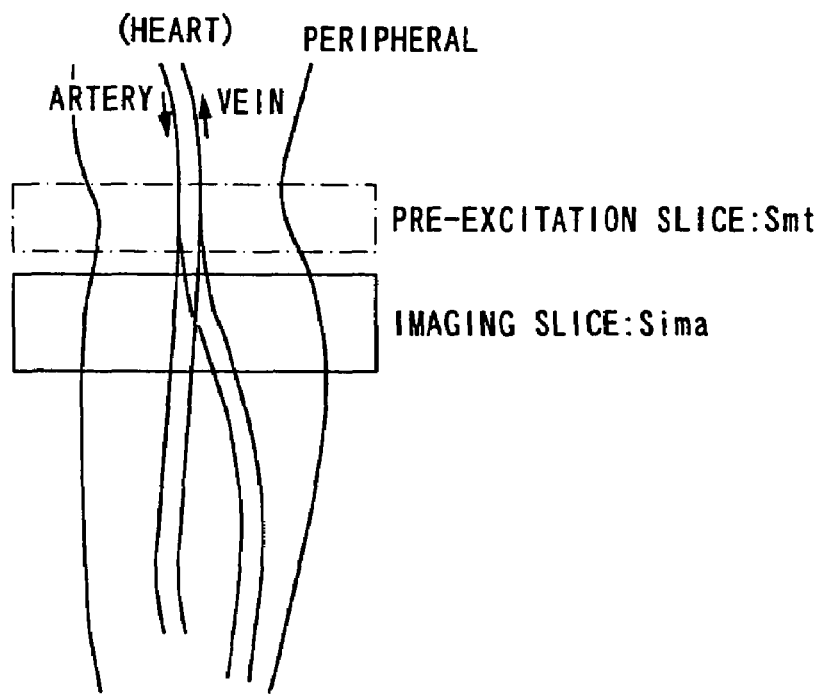
FIGS. 4A and 4B show the positional relationship between one slice to be imaged and the other slice to be pre-excited for each diagnostic region.
Figure 4B:
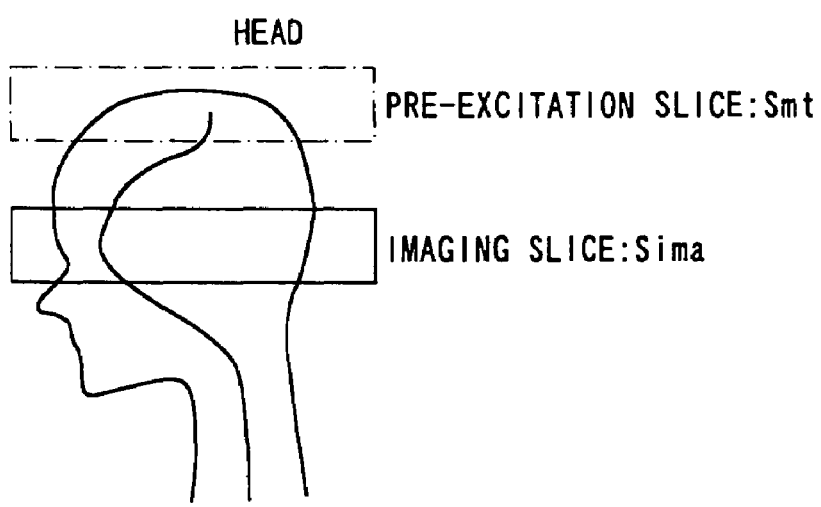
Figure 5:
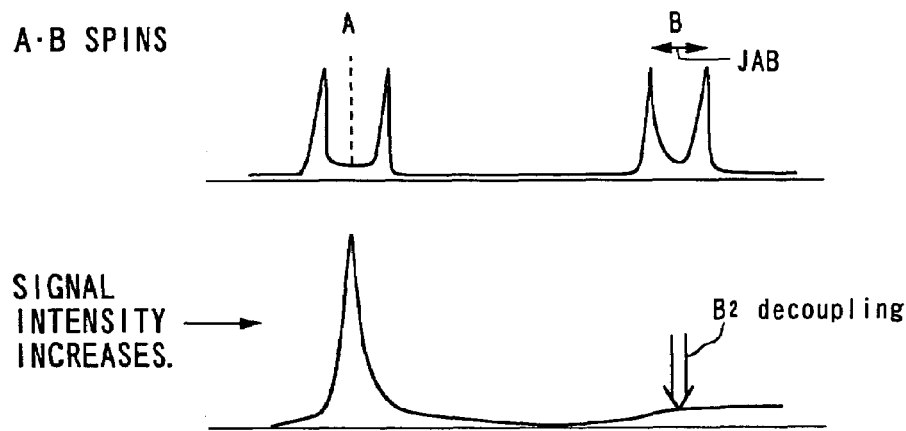
FIG. 5 illustrates decoupling between spins.

The slice gradients $G_S$ have a strength level of $G_{S1}$ that permits a selected slice to position at a different location from a slice $S_{ima}$, gapless or with a gap, as in FIGS. 4A or 4B.

Each MT pulse $P_1$ ($P_2, P_3, \ldots, P_n$) is formed by a sinc function, for example, and its pulse strength is set so that the flip angle FA becomes for example, 90 degrees. The total number of MT pulses $P_1, P_2, P_3, \ldots, P_n$ is ten, for example.

In this embodiment, instead of the conventional one MT pulse having a large flip angle FA (for example, 500 to 1000 degrees) applied slice-selectively, used are a plurality of divided pulses applied consecutively as an MT pulse train.

An flip angle FA given each MT pulse $P_1$ ($P_2, P_3, \ldots, P_n$) is a divided value (preferably, 90 to 100 degrees) set so that the entire MT pulse train is able to cause desired MT effects. The total number of MT pulses is assigned to an appropriate number (for example, 5 to 10 pieces) in consideration of MT effects given by the entire MT pulse train and a time required to complete the entire scanning (imaging). The duration of each MT pulse divided is as short as approx. 1300 μsec, which is largely shorter than the conventional slice-selective MT pulse.

A period of Δt between the divided MT pulses is determined so that MT effects for water/fat of parenchyma of a slice to which the MT pulses are applied (refer to FIG. 4) can be optimized. This period Δt depends on regions to be imaged, and if necessary, Δt=0 can even be set.

The gradient spoiler pulses $SP_S$, $SP_R$, and $SP_E$ to be applied in the slice, phase-encoding, and readout directions are used as end spoilers in the pre-sequence $SQ_{pre}$. Each gradient spoiler pulse dephases spins in each direction after a plurality of divided MT pulses have been applied, excluding spin mutual interference from the pre-sequence and the data acquisition sequence.

This is effective in preventing occurrence of stimulated echoes. This spoiler pulse can be applied only in any one or two direction.

The data acquisition sequence $SQ_{acq}$ is executed on an FSE method, for example, including a slice gradient $G_S$, read-out direction $G_R$, and phase-encoding direction $G_E$.

The host computer 6 executes a given main program, during which time it applies pulses on a pulse sequence shown in FIG. 3. This application of the pulses is done via the x, y, and z-coils $3x$ to $3z$ and the RF coil 7, under the control of the sequencer 5.

To begin with, in the pre-sequence $SQ_{pre}$, the divided n-piece MT pulses $P_1$ to $P_n$ (n is an integer larger than 1; for example, n=10) each having a flip angle FA of α degrees (for example, α=90 degrees) are applied in sequence with the slice gradient (=strength $G_{S1}$).

Suppose that a region to be diagnosed is the inferior limb, as shown in FIG. 4B. Appropriately setting the strength $G_{S1}$ of the slice gradient $G_S$ allows a pre-excitation slice $S_{mt}$ having a given thickness to be located in parallel and almost contiguously to the artery-inflowing side of a desired slice $S_{ima}$ to be imaged. Hence, the MT pulses divided into n-pieces are applied in turn every interval Δt apart.

Alternatively, adjusting the strength, for example, of the slice gradient $G_S$ may locate the pre-excitation slice $S_{mt}$ to the vein-inflowing side, that is, the artery-outflowing side of the imaging slice $S_{ima}$. Between the imaging slice $S_{ima}$ and the pre-excitation slice $S_{mt}$, there may be either a proper gap or gapless, depending on necessity.

Then, in the pre-sequence $SQ_{pre}$, the divided MT pulses are followed by the gradient spoiler pulses $SP_S$, $SP_R$, and $SP_E$ applied in the slice, readout, and phase-encoding directions, respectively.

Thus, at first, a plurality of divided MT pulses are applied to the pre-excitation slice $S_{mt}$. Namely, it is repeatedly excited during a shorter duration a plurality of times by the MT pulses with a smaller flip angle. This application gives rise to excitation of spins residing within the pre-excitation slice $S_{mt}$. This excitation becomes off-resonance against the imaging slice $S_{ima}$, thus providing the imaging slice $S_{ima}$ unique MT effects according to the present invention, which will be described later. Spins which have remained in the lateral magnetization after the application of the divided MT pulses are then dephased sufficiently by the spoiler pulses $SP_S$, $SP_R$, and $SP_E$.

After this, the data acquisition sequence $SQ_{acq}$ follows, where scanning is performed with the imaging slice $S_{ima}$ on an FSE method, for example, under the control of the sequencer 5. Because the slice gradient $G_S$ whose strength is $G_{S2}$ ($\neq G_{S1}$) is set this time, the imaging slice $S_{ima}$ is set at a desired location. A plurality of echoes responding to a plurality of refocusing RF pulses are acquired from the imaging slice $S_{ima}$ via the RF coil 7 and sent to the receiver 8R. A series of such processes is carried out every time of excitation.

Echo data acquired from a subject (patient) P are processed into digital forms, and sequentially stored into the arithmetic operation unit 10. This unit 10 is responsive to a reconstruction command from the host computer 6, so that a set of echo data mapped in the tow-dimensional Fourier space are tow-dimensionally Fourier-converted to produce MRA image data of the imaging slice $S_{ima}$.

This MRA image has less artifacts and a remarkably improved degree of image contrast between inflowing blood/parenchyma in comparison with the conventional MT pulse. This is thanks to use of a plurality of divided MT pulses according to the present invention. To be specific, this is because the echo signals form parenchyma (stationary portion) within the imaging slice $S_{ima}$ decrease owing to MT effects, while MT effects occurring in blood flow (arteries and/or veins) inflowing into the imaging slice $S_{ima}$ are reduced. That is, a plurality of divided short-duration MT pulses shorten the apparent T1 relaxation time of blood that is flowing and tumbling, leading to reduced MT effects. On the other hand, the parenchyma suffers a simple sum of a plurality of divided MT pulses, reducing the signals correspondingly to the sum. Therefore, compared to the conventional one MT pulse technique, image contrast between the inflowing blood and the parenchyma shows a greater improvement.

This feature is explained in detail from a principle viewpoint.

Considered herein are differences in MT effects giving flowing or tumbling blood between a fist case in which one RF pulse having a long duration is applied as the MT pulse and a second case in which a plurality of RF pulses each having a short duration are applied in sequence.

General factors that contribute to T1 relaxation time (T1) will be first explained. The time T1 changes depending on temperature, paramagnetic components, the size of molecules, their environments, viscosity and others, and can be expressed by the following factors in molecules constituting components.

$$1/T1 = 1/T1(DD) + 1/T1(SR) + 1/T1(SC) + 1/T1(CSA) + \ldots$$

In this expression, the first term T1 (DD) represents the internuclear dipole-dipole interaction. This interaction moves energy produced by RF excitation to lattices, as pictorially shown in FIG. 5, thereby decouple spins A and B of molecules coupled so as to increase signals.

The second term T1 (SR) represents the rotational move of spins. Molecules coupled move rotationally. Although depending on magnitudes of motion, molecules under rotational motion generate local magnetic fields, thereby contributing to shorted T1.

The third term T1 (SC) represents scaler coupling. When one atom coupled with quadrupole (atoms satisfying the spin quantum number I≧1; for example, $O^{17}=5/2$, $m_n^{55}=5/2$; as a reference, $H^1=1/2$), the quadrupole has an inherent shorter relaxation time referred to as a quadrupole relation. Spins coupled with the quadrupole are also reduced in their T1 relaxation time.

And the fourth term T1 (CSA) is a term called chemical shift anizotoropy, which represents changes in local fields on changes in electronic shielding effects. This also affects the T1 relaxation time.

Thus, the T1 relaxation time depends on various factors. The foregoing factors are not all, but major ones to affect the T1 relaxation time.

Even in stationary blood, oxyhemogrobin and deoxyhemogrobin have paramagnetic ions (primarily, iron I and iron II), so producing local magnetic fields to reduce the T1 relaxation time. In addition, in terms of the T2 relaxation time, the presence or absence of $O_2$ has influence on veins (with oxygen; T2=120 msec) and arteries (less oxygen; T2=220 msec).

Figure 6:
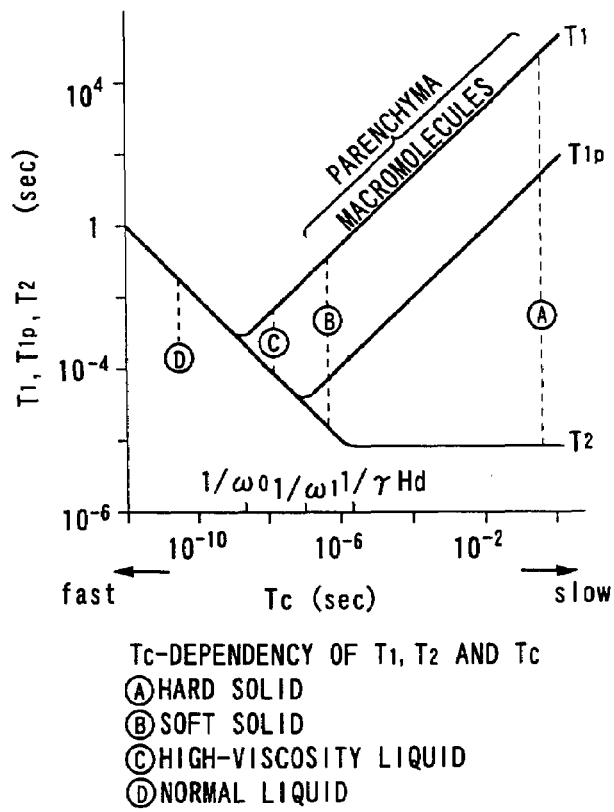
FIG. 6 shows Tc-dependency of T1 relaxation time and others.

FIG. 6 shows the dependency of T1, T2, and T1P on Tc (i.e., effective correlation). In the graph, a position A shows Tc of hard solid, another position B does that of soft solid, another position C does that of liquid of a high viscosity, and another one does that of ordinary liquid (refer to "T. C. Farrar and E. D. Becker, Pulse and Fourier Transform NMR, P.98, Academic Press(1971)").

Tc, which is called effective correlation, is a factor representing motion of molecules. To be specific, it represents the degree of tumbling (rotation and vibration) of fast-moving molecules. In FIG. 6, as proceeding to the right along the lateral axis, the degree of solid gets higher, so molecules move slower. On this relationship, it is understood that the T1 relaxation time differs between fast-moving blood and stationary blood.

Moreover, the application of a plurality of divided MT pulses causes flowing blood to shorten its apparent T1 relaxation time.

MT effects are, as described before, a phenomenon by which, when the equilibrium between free water Hf and macromolecules Hr which are neighboring to each other and in dipole-dipole interaction, protons of the macromolecules are excited, by an RF pulse of which frequency is off-resonance against free water, so that signal intensities of free water that interferes with protons are affected. When taking the magnetization of free water is as Hf and that of macromolecules is as Hr, and constants of reaction time are $k_1$ and $k_{-1}$, the relation of

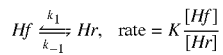

is obtained. Here, the square brackets show concentration and K is a reaction constant.

Therefore, when letting the T1 relaxation time of free water be $T1f$ and that of macromolecules be $T1r$, $$R1f = \frac{1}{T1f}, \quad R1r = \frac{1}{T1r}$$

are obtained. Where $M_{f(t)}$ is the magnetization of free water at time=t, $M_{f(0)}$ is that of free water at time=0, $M_{r(t)}$ is that of macromolecules at time=t, and $M_{r(0)}$ is that macromolecules at time=0, $$\frac{dM_{f(t)}}{dt} = (M_{f(0)} - M_{f(t)}) \cdot R1f - M_{0(t)} \cdot k_1 + M_{r(t)} \cdot k_{-1}$$

is obtained.

Magnetization $M_{fSAT}$ realized when the MT pulses are applied is expressed by $$M_{fsat} = \frac{M_{f(0)}}{1 + k_1 \cdot T1f}$$

, and its longitudinal relaxation time $T_{1SAT}$ is expressed by $$\frac{1}{T_{1SAT}} = R1f + k_1$$

Therefore, the reaction constant $k_1$ is $$k_1 = \frac{1}{T_{1SAT}}\left(1 - \frac{M_{fSAT}}{M_{f(0)}}\right)$$

, where $T_{1SAT}$ is an apparent T1 (refer to "Balaban, Magn. Reson. Quarterly Vol. 8, No. 2, 1992").

When expressing the magnetization of protons of free water in moving blood as HfA, that of macromolecules in moving blood as HrA, that of free water in stationary parenchyma as HfB, and that of macromolecules in stationary parenchyma as HrB, the magnetization behaves as pictorially shown in FIG. 7, in response to the application of the MT pulses according to the present invention.

When the first divided MT pulse P1 (whose flip angle is 100 degrees, for example) is applied to the magnetization HfA and HrA which are in equilibrium within moving blood (FIG. 7A), magnetic spins (magnetization) are transferred from the macromolecule magnetization HrA (nuclear pool) to the free water magnetization HfA (nuclear pool). To the contrary, energy is transferred from the free water magnetization HfA to the macromolecule magnetization HrA (see FIG. 7B). Because a divided MT pulse is applied, amounts of transferred spins and energy are both small, thereby providing low MT effects.

Owing to the longitudinal relaxation that follows the excitation, the macromolecule magnetization HrA returns to its initial equilibrium state. In the course of the return process, the T1 relaxation time T1 is apparently shortened due to such factors as the dipole-dipole interaction and the paramagnetic effects, speeding up the return process of the magnetic spins HrA.

Such divided MT pulses $P_2, P_3, \ldots, P_n$ are applied in succession to the first one $P_1$. The entire MT effects are apparently lowered because of their shortened T1 relaxation time (refer to FIGS. 7C and 7D). Consequently, compared to stationary or almost motionless blood and parenchyma, MT effects occurring in flowing (moving) blood are smaller, thus echo signals from an imaging slice $S_{ima}$ are raised in intensity.

Figure 1A:
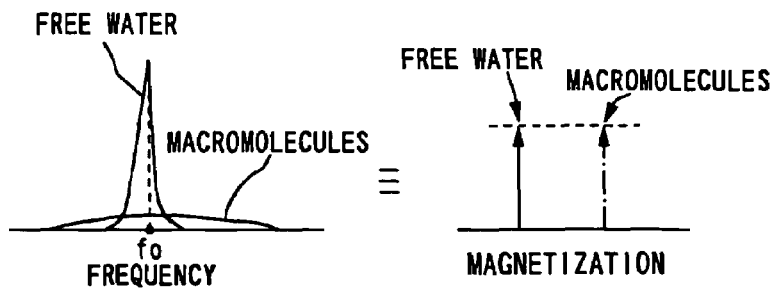
FIGS. 1A to 1C illustrate MT effects according to the conventional MT pulse.
Figure 1B:
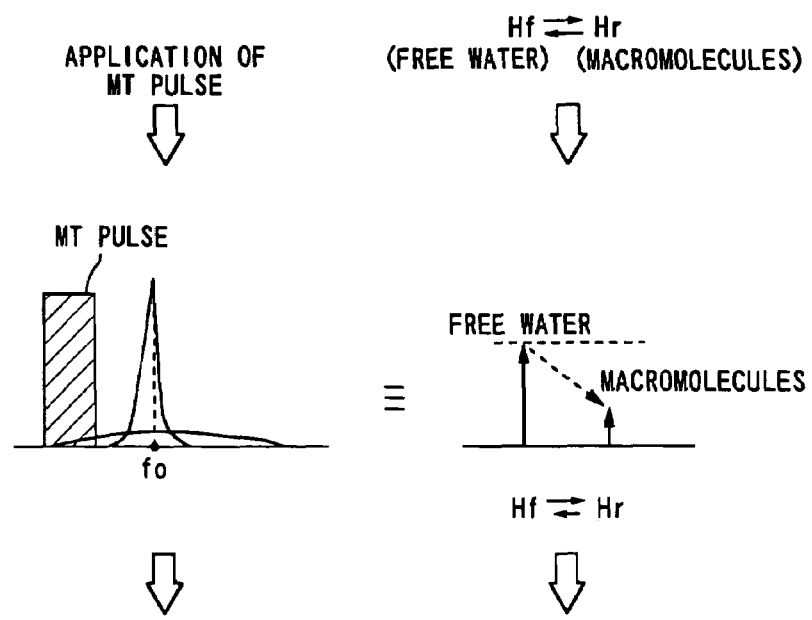
Figure 1C:
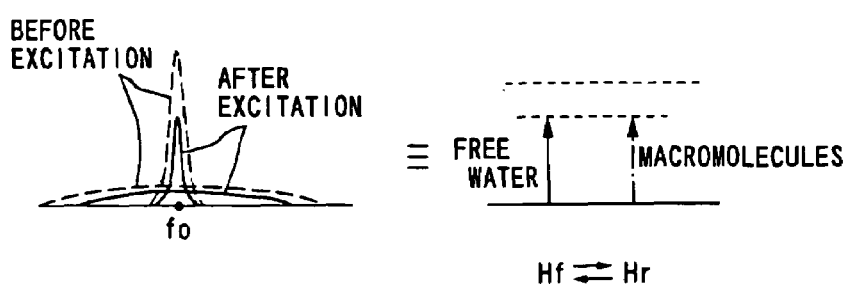

In contrast, MT effects occurring both the free water magnetization HfB and the macromolecule magnetization HrB of stationary or almost motionless parenchyma can be expressed with the foregoing FIG. 1. In other words, a plurality of divided MT pulses serve only the sum of their magnetization HfB and HrB. Thus, the parenchyma of the imaging slice $S_{ima}$ has the equivalent MT effects to the conventional MT effects, which reduces echo signal intensities, as seen in the conventional MT pulse.

Accordingly, the MRI system is able to utilize slice-selective divided MT pulses to make a distinction between stationary or almost motionless objects and moving objects. Compared to the conventional one MT pulse whose duration is long and whose flip angle is large, contrast between blood (blood flow) and parenchyma of an imaging slice can be improved greatly, providing a higher depiction performance of blood flow. Therefore, a higher quality of MRA images can be provided.

In this embodiment, owing to the fact that the MR contrast medium is not used for obtain MRA images, non-invasiveness is still kept. Compared to MRA imaging with contrast mediums, less physical and mental burdens are given patients.

Concerning this embodiment, variations can be provided as follows. In the pulse sequence shown in FIG. 3, a plurality of slice gradient pulses $G_S$ are applied concurrently with a plurality of divided MT pulses. This pulse train may be changed, however, as shown in FIG. 8, wherein only a one slice-gradient pulse $G_S$ is continuously applied over the entire application period of a plurality of divided MT pulses. This manner can shorten a time necessary for applying the MT pulse train $P_{MT}$, realizing a shorter imaging time.

Figure 9:
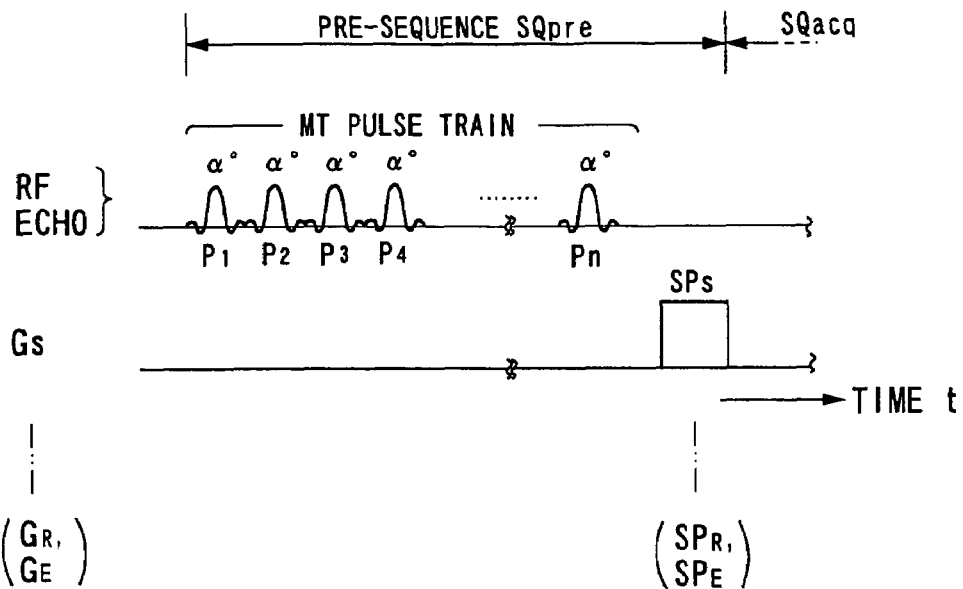
FIG. 9 is part of a pulse sequence showing another example of applying divided MT pulses.

Another variation for applying a plurality of divided MT pulses is shown in FIG. 9. According to this application, no gradient pulse is applied in any of the slice, readout, and phase-encoding directions; a plurality of divided MT pulses are first applied alone, then gradient spoiler pulses are applied in any one or more of the slice, readout, and phase-encoding directions. Thus the divided MT pulses are applied in a slice-non-selective fashion, and effective in a wider area, not limited to whether a region to be imaged is a slice or slab. In foregoing FIGS. 8 and 9, gradient pulses including spoiler pulses in the readout and phase-encoding directions are omitted from being drawn.

Still, data acquisition sequences available to the MRI system is not limited to the foregoing FSE sequence, but may include other types of pulse sequences based on various methods, such as FE, SE, EPI, FLAIR, or FASE methods.

Second Embodiment

Referring to FIGS. 10 to 17, a second embodiment of the present invention will be described.

In this embodiment, using a plurality of divided MT pulses described above, the parenchyma of the lungs of a patient will be imaged.

For MR-imaging the lungs, three approaches have been known primarily, which are to use a hyper-polarized gas (e.g., xenon or helium), to perform a perfusion imaging using a contrast medium Gd-DTPA (refer to "Hatabu H, et al., MRM 36:503-508, 1996"), and to perform imaging with suction of oxygen using oxygen molecules (refer to "Edelman RR, et al., Nature Medicine 2, 11, 1236-1239, 1996).

Of these, the first approach is based on imaging at the MR frequency of, for example, a xenon gas (Xe) suctioned into the lungs. The second one is a technique to observe a perfused state of Gd-DTPA in blood. The third one utilizes a report that oxygen molecules, which are weakly paramagnetic, cause a signal from water to change sufficiently at the surface of the pulmonary alveolus, the water signal being observable by MRI.

However, the first approach needs an ordinary xenon gas to be hyper-polarized, leading to a high cost for producing the gas. The second one that uses an MR contrast medium for perfusion imaging requires an invasive treatment against patients. Mental and physical burdens of patients are enormous, in addition to a high examination cost. In some cases, a patient's specific character shows the rejection against MR contrast medium. Moreover, the third one with the suction of oxygen molecules is difficult to gain sufficient signal changes in an image, no providing images as satisfactory as it could be used for research or distinct contour information.

The lungs are constructed such that most of their surfaces are occupied by the spongy pulmonary alveolus, bronchus, pulmonary artery, and pulmonary vein surrounded by air. The surface of the spongy pulmonary alveolus amounts to a huge area, but it dose not have free water inside and outside the cells, unlike other organs (such as the liver and ren). Thus, in the case of the lungs, the signal of water, which is an objective to be detected in MRI, is only detected from their blood systems, so the water signal from the parenchyma thereof is absolutely short. Therefore it is considered that a region surrounding the pulmonary alveolus is difficult to be reflected into MR signals, because of shortage of water molecules compared to an amount of their surfaces, although the lungs have a T2 value of 80 msec comparable to other organs (refer to "JMRI, 2(S):13-17, 1992"). As a result, the conventional MR imaging was required to use MR contrast mediums.

This embodiment utilizes fully the advantages of a plurality of divided MT pulses so that the parenchyma of the lungs, which has been difficult to be imaged with no contrast medium, is imaged.

An MRI system of this embodiment is configured similarly to that of the first embodiment, but different from the first one in scan procedures as below.

Figure 10:
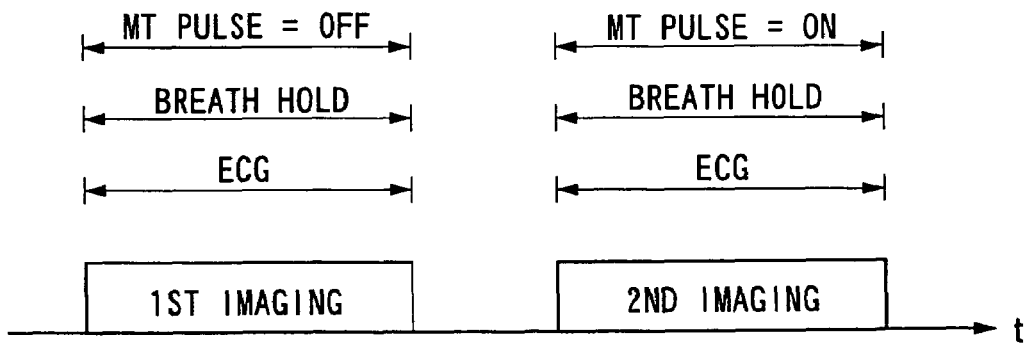
FIG. 10 pictorially shows the temporary relationship of two times of imaging according to a second embodiment.

Succeedingly to a preparation work including a not-shown positioning scan and the input of imaging conditions, the host computer 6 performs imaging at least two times. Such imaging is performed two times, for example, as shown in FIG. 10, in each of which is a two- or three-dimensional scan that acquires a set of echo data necessary for image reconstruction. It is preferred that each scan be performed with a patient's breath hold and an ECG gating technique.

A pulse sequence available for this imaging may be a two-dimensional or three-dimensional scan, but should be based on a Fourier transform method. Its pulse train may use an SE, FSE (Fast SE), FASE (Fast Asymmetric SE), FE, FFE(Fast FE), segmented FFE, EPI (Echo Planar Imaging), and other method.

In addition to the reconstruction processing of raw data, the arithmetic operation unit 10 can perform synthesis processing and difference processing of image data. Such synthesis processing includes addition of a plurality of frames of image data pixel by pixel, maximum intensity projection (MIP) for selecting maximums along rays through a set of three-dimensional image data, and others. Alternatively, the image data synthesis processing can be performed by adding as-acquired raw data to each other with the axes of a plurality of frames matched with each other in the Fourier space. In addition, the addition includes simple addition, averaging, weighted addition, and others.

The storage-unit 11 is able to store not only reconstructed image data but also synthesized (or difference) image data. The input device 13 is used to provide the host computer 6 desired imaging conditions, the type of pulse sequence, information notifying the image synthesis processing or difference processing.

The operation of the MRI system will now be described with reference to FIGS. 10 to 17.

As shown in FIG. 10, the host computer 6 performs imaging two times using a three-dimensional (3D) FASE method employed as one example. The first imaging is carried out with breath hold and ECG-gating techniques, but with no application of a plurality of divided MT pulses (MT pulses=off). The second imaging starts at an appropriate moment after the first imaging terminated.

Like the first imaging, the second imaging uses breath hold and ECG-gating techniques, in addition to application of a plurality of divided MT pulses (MT pulses=on).

Figure 13:
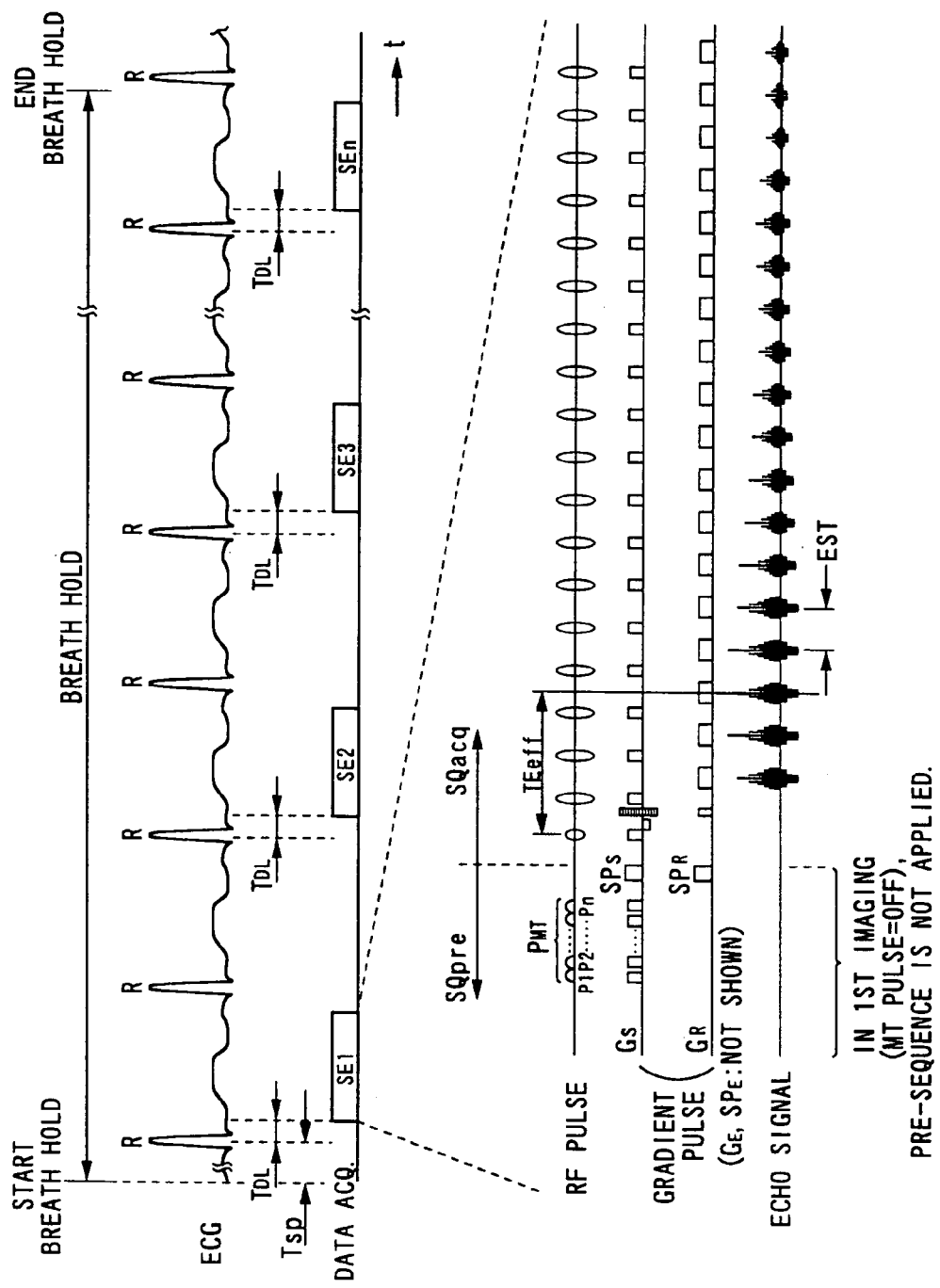
FIG. 13 is a pulse sequence showing two times of imaging based on ECG gating.

FIG. 13 exemplifies a pulse sequence used in both the first and second imaging scans. The pulse sequence is based on a three-dimensional FASE method (Fast Asymmetric SE method made by an FSE method with a half-Fourier technique). In FIG. 13, the phase-encoding gradients including a spoiler pulse are not shown.

In the case of the first imaging, a data acquisition sequence $SQ_{acq}$ shown in FIG. 13 is only applied, while a pre-sequence $SQ_{pre}$ is not used, though FIG. 13 shows the pre-sequence (FIG. 13 shows both the cases for the first and second imaging). That is, an MT pulse train $P_{MT}$ and gradient spoiler pulses $SP_S$, $SP_R$, and $SP_E$ that compose the pre-sequence $SQ_{pre}$ are not applied in the first imaging. Scanning in the first imaging is performed without the MT pulses (off).

In contrast, for the second imaging, as shown in FIG. 13, prior to the data acquisition sequence $SQ_{acq}$, the pre-sequence $SQ_{pre}$ is applied. Thus a plurality of divided MT pulses are applied that are formed in the same way as in the first embodiment.

Alternatively, although not shown in FIG. 13, the pulse sequence used in the second imaging may be constructed such that, with the slice selection for the RF pulses of the data acquisition sequence $SQ_{acq}$ is unchanged, gradients for selecting a region to which the divided MT pulses are applied are also applied to the phase-encoding and readout directions, in addition to the slice direction.

As one example, in the three-dimensional FASE pulse sequence shown in FIG. 13, the effective echo time $TE_{eff}$ and the echo train spacing are set to 100 msec and 5 msec, respectively. As to the divided plural MT pulses, the frequency offset of 1300 Hz and five divided MT pulses are set (a total flip angle of the five divided MT pulses is 800 degrees, for example). Further, the repetition time TR is 3247 msec, the flip angles of flip/flop pulses are 90/140 degrees, the matrix size is 256×256, and the FOV (field of view) is 37 cm×37 cm. When considering the fact that the vessels of the lungs run in all the directions therein, it is preferred that scanning for each imaging is performed a plurality of times as the phase-encoding direction is changed each time, and data acquired each time are subject to their averages pixel by pixel. This technique (called SPEED technique) of combining swapping the phase-encoding direction and averaging has been disclosed by "J. of Magn. Reson. Imaging (JMRI) 8: 503-507, 1998." For instance, scanning is performed two times with the phase-encoding direction altered by 90 degrees and data acquired each time are averaged to produce image data in each time of imaging.

First, the first imaging is carried out as below. The host computer 6 executes the processing shown in FIG. 11 in response to operative information from the input device 13.

Specifically, the host computer 6 reads from the input device 13 an optimum ECG-gating delay time $T_{DL}$ appropriately determined or selected by the operator (Step S20).

Then, the host computer 6 inputs scan conditions (for example, the direction of phase encode, an image size, the number of times of scans, a standby time between scans, and a pulse sequence dependent on a region to be scanned, and others) and information about image processing (addition, MIP, or others), converts those bits of information into control data, and outputs the control data to the sequencer 5 and arithmetic operation unit 10 (step S21).

If it is then judged that an instruction indicating the completion of preparations has been issued (step S22), a command indicating the start of a breath hold is output to the voice generator 16 (step S23). This causes the voice generator 16 to utter a voice message saying "Hold your breath, please." In response to this message, the patient holds her or his breathing.

Figure 12:
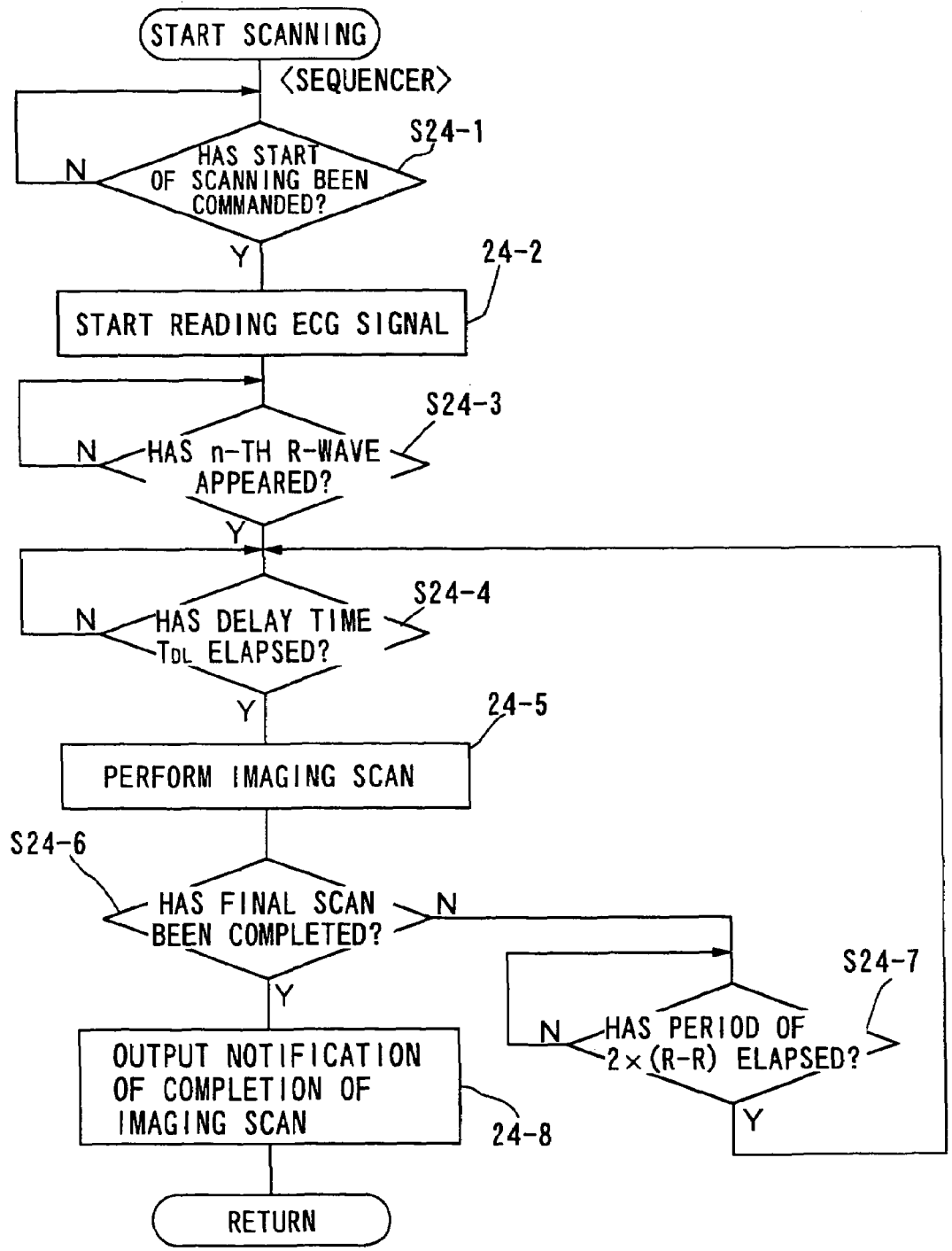
FIG. 12 outlines a flowchart exemplifying imaging procedures with ECG gating.

After commanding the start of the breath hold, the host computer 6 orders the sequencer 5 to start imaging (step S24; refer to FIG. 12).

As shown FIG. 12, when receiving the command for starting imaging (step S24-1), the sequencer 5 starts to read an ECG signal (step S24-2), and determines a predetermined n-th R-wave peak (reference wave) that appears in the ECG signal by observing an ECG triggering signal synchronous with the peak (step S24-3). The reason the appearance of the n-th R-wave (for example, n=2) is waited is to obtain a steady state of the breath holding. This waiting technique produces an adjusting time $T_{sp}$ shown in FIG. 13.

When the n-th R-wave peak appears, the processing is brought into a waiting period corresponding to the predetermined delay time $T_{DL}$ (step S24-4). The delay time $T_{DL}$ has been optimized such that the echo signal strength is the highest for imaging the pulmonary tissue, and its depiction performance is superior.

Figure 14:
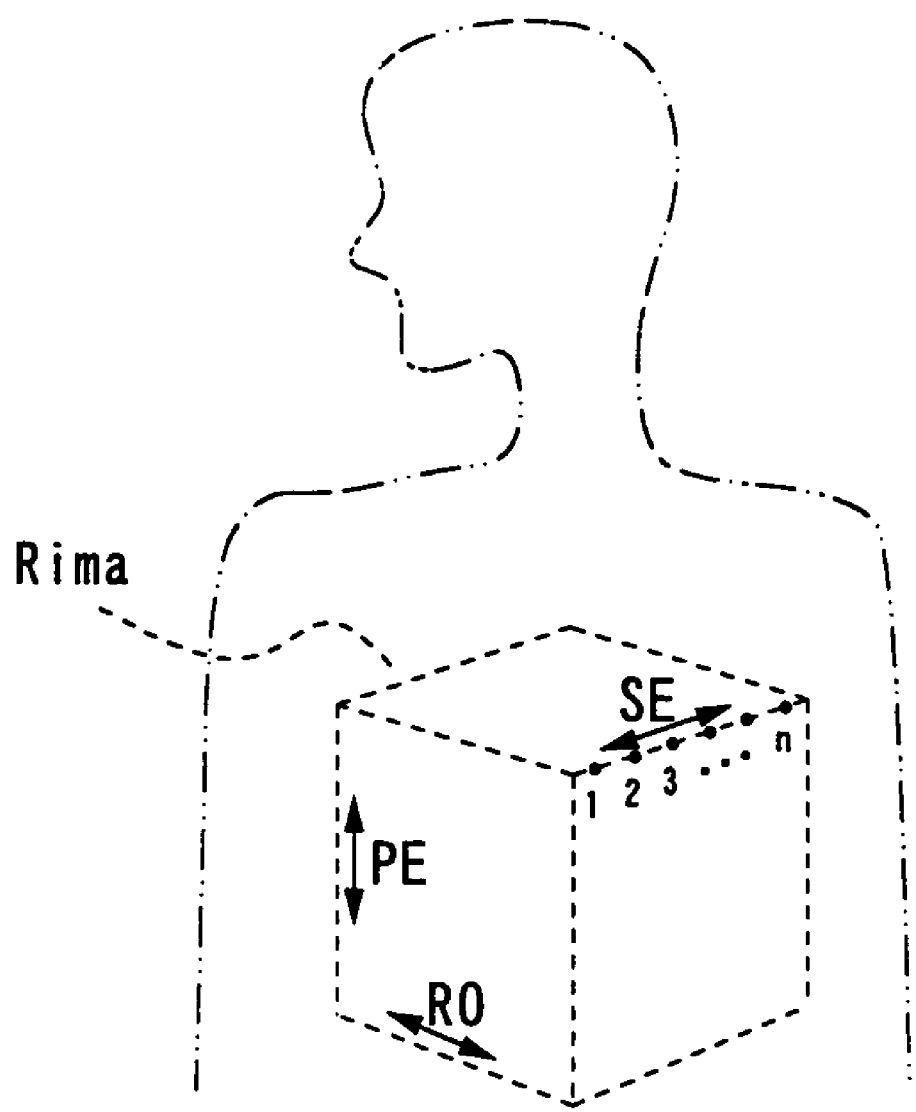
FIG. 14 illustrates the relationship between a three-dimensional region to imaged and slice-encoding, phase-encoding, and readout directions.

As it is determined that a time instant when the delay time $T_{DL}$ elapsed corresponds to an optimum ECG-gating time, the sequencer 5 starts scanning (step S24-5). Specifically, the sequencer 5 drives the transmitter 8T and gradient power supply 4 according to pulse-sequence information that has already been transmitted and stored, and executes the first scanning on the three-dimensional FASE-based pulse sequence with the ECG gating, as shown in FIG. 13. In this scanning, the MT pulse train $P_{MT}$ is not applied in the pre-sequence $SQ_{pre}$ (that is, MT pulse=off). By this scanning, echo signals are acquired from a three-dimensional region containing the lungs, as illustrated in FIG. 14, for an interval of about 600 msec under an amount SE1 of the first slice encoding.

After the completion of the first scanning under the one slice-encoding amount $SE_1$, the sequencer 5 determines whether scanning under the final slice-encoding amount $SE_n$ was finished or not (step S4-6). If the determination is NO at this step, the processing undergoes a waiting process for a relatively shorter interval (for example, 2 heart beats; 2R-R) from the R-wave used for the scanning as monitoring the ECG signal (step S24-7). This shorter waiting process deliberately suppresses the relaxation of the longitudinal magnetization of spins in the stationary parenchyma. This waiting time determines the repetition time TR.

In response to the appearance of the third R-wave (YES at step S24-7), the sequencer returns its processing to the foregoing step S24-4. Therefore, scanning is performed in the same way as above, under the second slice-encoding amount $SE_2$, from a time instant when the specified delay time $T_{DL}$ passed from a ECG triggering signal representing the third R-wave peak (steps S24-4, 5). This scanning also allows the acquisition of echo signals from the three-dimensional region $R_{ima}$. Likewise, such scanning is repeated to acquire echo signals until the final slice-encoding amount $SE_n$ (for example, n=8).

When the final scanning has been finished, the determination performed at step S24-6 becomes YES, the sequencer 5 informs the host computer 6 of the completion of the scanning (step S24-8). Thus, the processing is returned to the host computer 6.

Figure 11:
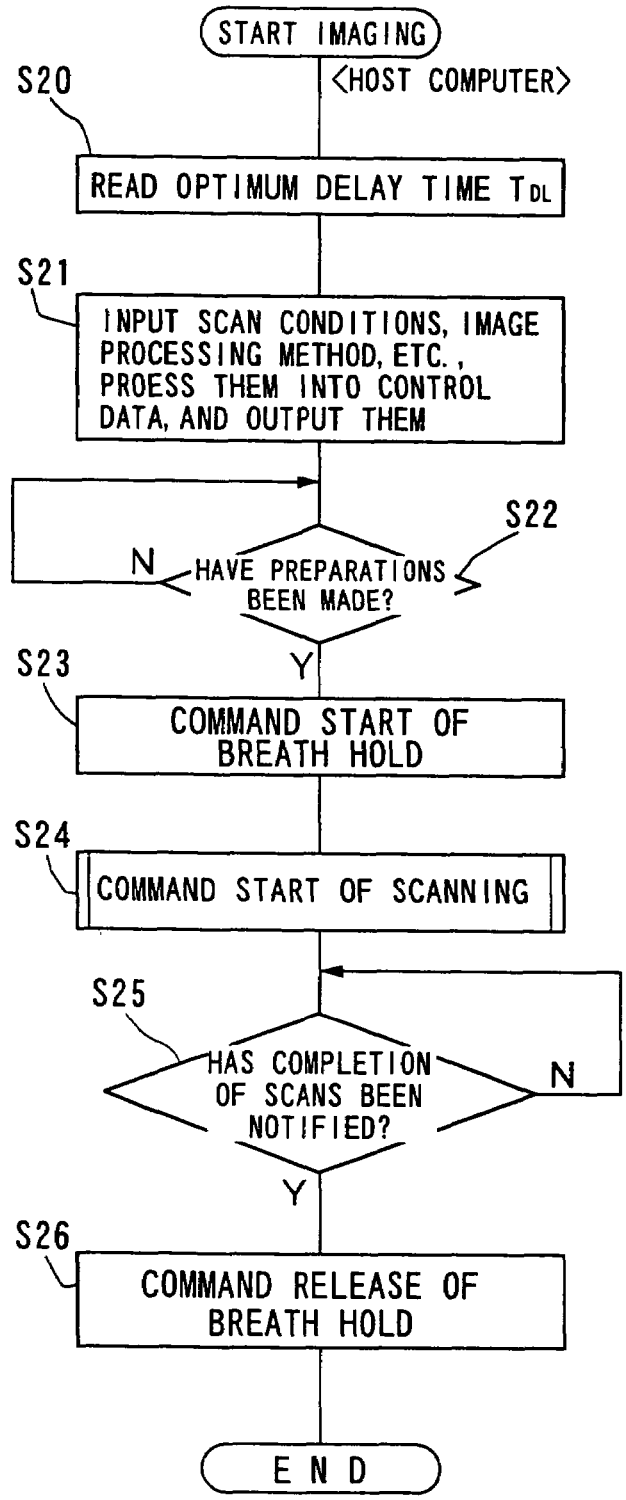
FIG. 11 outlines a flowchart exemplifying procedures for the first imaging, which are executed by the host computer.

The host computer 6, when receiving the completion of the scanning from the sequencer 5 (step S25; FIG. 11), outputs a command of release of the breath hold to the voice generator 16 (step S26). The voice generator 16 then utters a voice message saying, for example, "You can breathe." toward the patient. This will terminates the interval of the breath holding.

Therefore, as illustrated by FIG. 13 sequence, on the basis of the ECG-gating technique of every 2R-R, the scanning is performed n-times (for example, n=8) for each slice-encoding amount. A duration required for these n-time scans, that is, an interval that a patient is required to continue breath holding, is 20 to 25 seconds, as one example, although this interval depends on imaging conditions.

Spin echo signals produced in the patient P for each scan are received by the RF coil 7, and sent to the receiver 8R. The receiver 8R performs various kinds of pre-processing with the spin echo signals. The signals are thus converted into digital quantities. The digital echo data are sent to the arithmetic operation unit 10 via the sequencer 5 and mapped in a three-dimensional image k-space formed in its incorporated memories. Because this embodiment is based on the half-Fourier method, data in the k-space that are not acquired are computed using the already acquired data, and additionally mapped in, providing the full echo data in the whole k-space.

When a predetermined standby time passes after the first imaging, the second imaging is performed in the similar manner to that described by FIGS. 11 and 12. Only a difference from the first one is that, at step S21 in FIG. 11, information about applying the MT pulse train $P_{MT}$ (MT pulses=on) in the pre-sequence $SQ_{pre}$ is provided to the host computer 6, and such control data as scan conditions including the information, image processing method and others given to the sequencer 5. The other scanning conditions are the same as those in the first imaging. Thus, the pulse sequence on the three-dimensional FASE method performed at step S24-5 in FIG. 12 includes a pre-sequence $SQ_{pre}$ and a data acquisition sequence $SQ_{acq}$, as shown in FIG. 13. Namely, a plurality of divided MT pulses are added at the front of each scan.

Hence, echo data acquired by this second imaging are also mapped in the image k-data in the same way as that in the first imaging.

When the data acquisition processing is completed in such way for the two times of imaging, the host computer 6 commands the arithmetic operation unit 10 to process and display of image data. A series of these processes are shown in FIG. 15.

Figure 15:
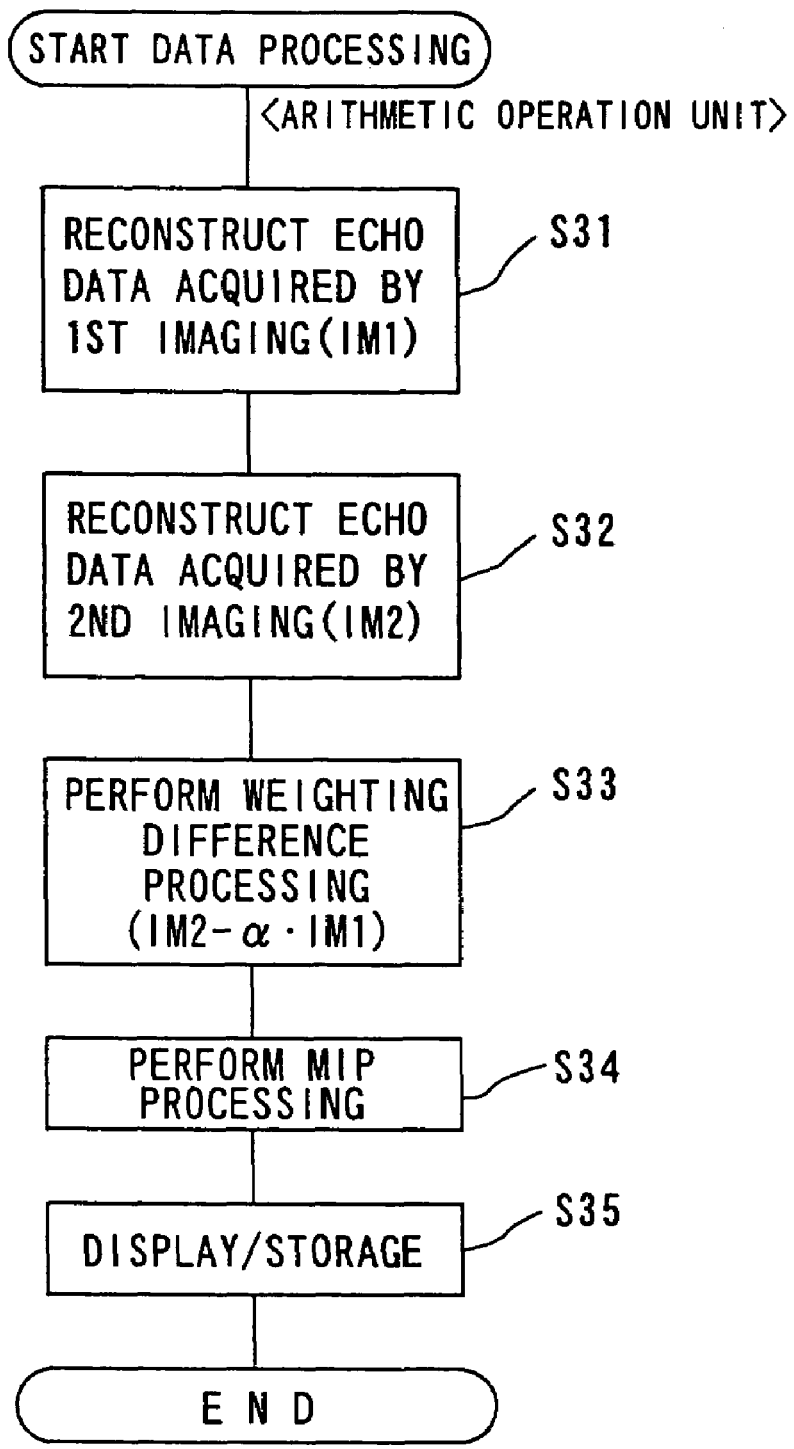
FIG. 15 is an outlined flowchart showing an example of data processing carried out after echo acquisition.

The arithmetic operation unit 10 performs a three-dimensional transform with echo data in the k-space acquired and mapped by the first imaging, thereby reconstructing absolute-value image data IM1 in the real space (FIG. 15, step 31). Likewise, for those acquired and mapped by the second imaging, the same reconstruction as above is performed to provide absolute-value image data IM2 reconstructed into the real space (step 32).

FIGS. 16A and 16B pictorially show signal levels of image data in pulmonary axial images produced on this embodiment (for sake of convenience, the both are shown as two-dimensional images). FIG. 16A shows an image IM1 when the MT pulses are turned off, while FIG. 16B does another image IM2 when the MT pulses are turned on. In the case of FIG. 16B, on account of MT effects accompanied with the application of the divided MT pulses, the signal values are lowered, but, when such lowering is compared between the parenchyma and the blood, the parenchyma is greater in degrees of such lowering than the blood. In FIG. 16B, only narrow hatching lines pictorially show the parenchyma portion where the degrees of the lowering a greater.

Figures 17A, 17B:
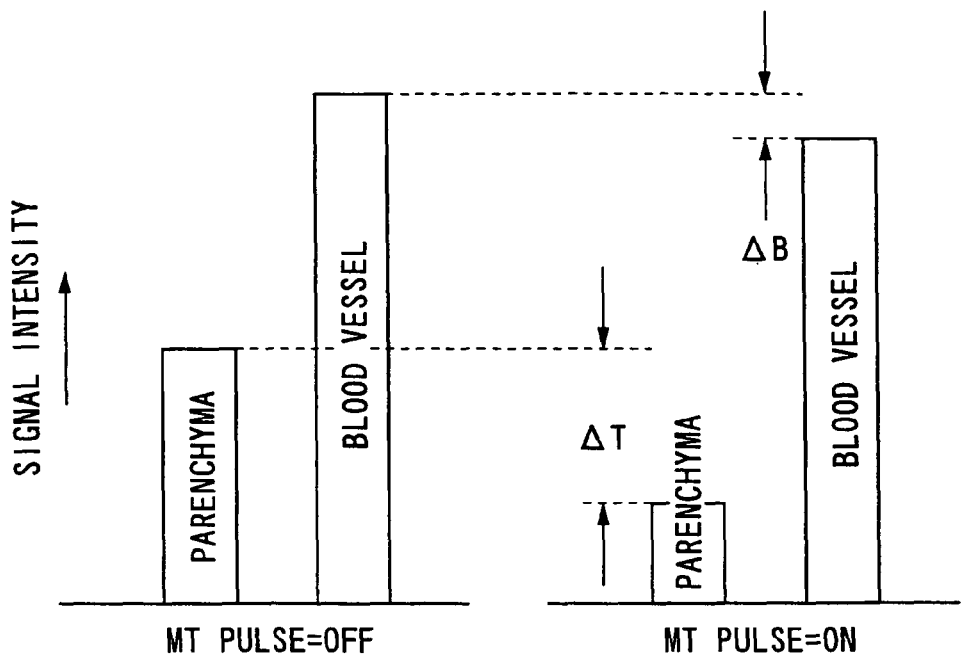
FIG. 17 is an illustration explaining differences in MT effects between parenchyma and blood.

More detailed explanation about such comparison will be given using FIGS. 17A and 17B. Because the MT pulses are turned off for the first image IM1, the signal levels in the tissue and blood of the lungs LG are determined into certain values depending on imaging conditions. The second image data IM2 are, however, obtained with the divided MT pulses. Therefore, the parenchyma of the lungs LG has larger MT effects than that occurring in the blood. Thus, as illustrated in FIG. 17B, a ratio ΔT between reduced signal levels for the parenchyma is larger that ΔB for the blood. This difference "ΔT−ΔB" between the ratios ΔT and ΔB contributes image data of the parenchyma of the lungs LG.

Hence, using a properly selected coefficient α ($0<α\leq1$), the arithmetic operation unit 10 performs pixel by pixel a difference operation of "IM1−α·IM2" with both the absolute-value image data IM1 and IM2 (FIG. 15, step S33). The resultant image data IM3 are illustrated in FIG. 16C (for sake of convenience, illustrated by a two-dimensional image). As shown therein, the signals in the blood of the lungs LG are almost cancelled out due to the difference computation, leaving only the parenchyma in the image IM3.

Then, a maximum intensity projection (MIP) process is done with thus-produced three-dimensional real-space image data IM3, producing a two-dimensional image data (FIG. 15, step S34). Such image data are not merely displayed by the display unit 12 but also stored in the storage unit 11. The three-dimensional image data IM3 are stored therein as well (step S35).

As described above, since a plurality of divided MT pulses used by the MRI system of this embodiment operate just as the sum of MT pulses for the stationary or almost stationary lung parenchyma, giving it larger MT effects. Compared with blood flow in the lungs, the signal value of their parenchyma is reduced largely. Thus, difference processing (simple or weighting difference processing) with an image obtained with no MT pulse can image the parenchyma of the lungs. Although it was thought before that imaging the parenchyma of the lungs without using gases, contrast mediums, or oxygen was impossible, it can preferably be imaged by the present embodiment.

Particularly, there is no need for injecting contrast mediums into patients, so non-invasive imaging can be done and mental and physical burdens given patients are remarkably relieved. Concurrently with it, an operator is free from cumbersome operations inherent to the contrast medium method, such as it is necessary to measure a time for best obtaining contrast effects. Moreover, differently from the contrast medium method, imaging can repeatedly performed easily by this embodiment, if necessary. In terms of imaging cost, this embodiment is advantageous because a high-cost contrast medium or gas is not used.

In the present embodiment, the gradient spoiler pulses are applied only one time at the last after a plurality of MT pulses last in turn. This application enables less (or almost zero) standby time between two neighboring MT pulses. Thus, the longitudinal relaxation of magnetization between two MT pulses is kept to a small quantity, thereby producing larger signal values.

Furthermore, the repetition time TR and the train spacing can be set to shorter lengths and the slice direction can be set in the front/back direction of a patient. Thus, the entire scan time can be reduced. The number of times of slice encodes may be less because of a shorter imaging length in the slice direction. The whole imaging time is shortened greatly compared to the conventional TOF or phase contrast method. A patient throughput is increased.

In addition, scanning for each of two times of imaging (scanning for obtaining a set of objective echo data) can be accomplished within one time of possible breath holding, relieving a burden on a patient. Further, suppressed are motion artifacts due to cyclic motions of the lungs and the like or due to the shifts of the body itself over a plurality of times of breath holding scans. Thus, less-artifact images can be provided.

Moreover, the use of the ECG gating can provide images from which motion artifacts caused by the motions of the heart are almost adequately excluded.

By the way, according to the ECG gating according to this embodiment, scanning is constructed so as to begin at a time phase delayed from an R-wave by a certain delay time $T_{DL}$. Alternatively, the time phase to start scanning may be set to other time phases depending on individual clinical demands.

Third Embodiment

Figure 18:
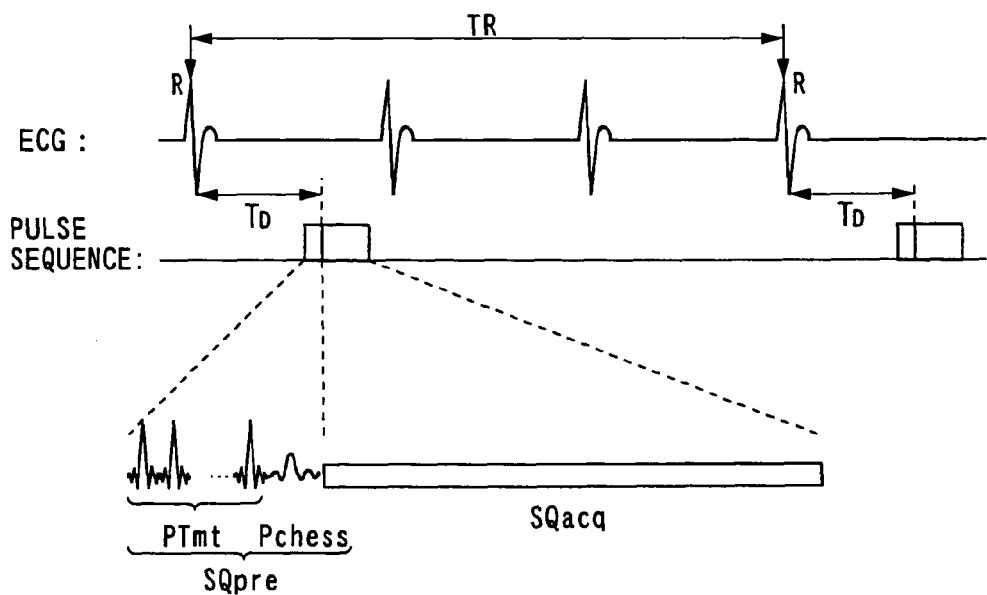
FIG. 18 is an outlined pulse sequence according to a third embodiment of the present invention.
Figure 19:
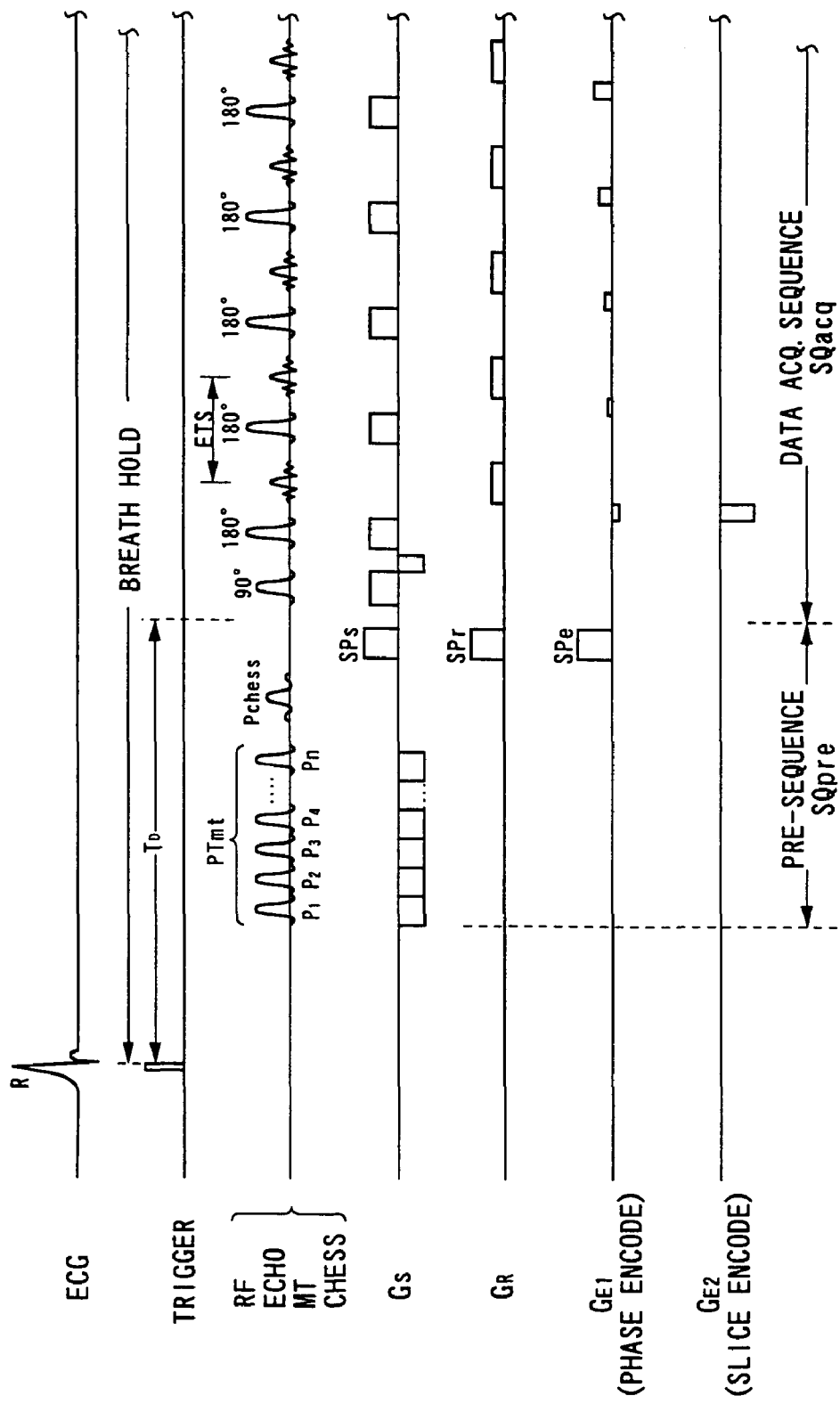
FIG. 19 is a partial detailed pulse sequence shown in FIG. 18.
Figure 20:
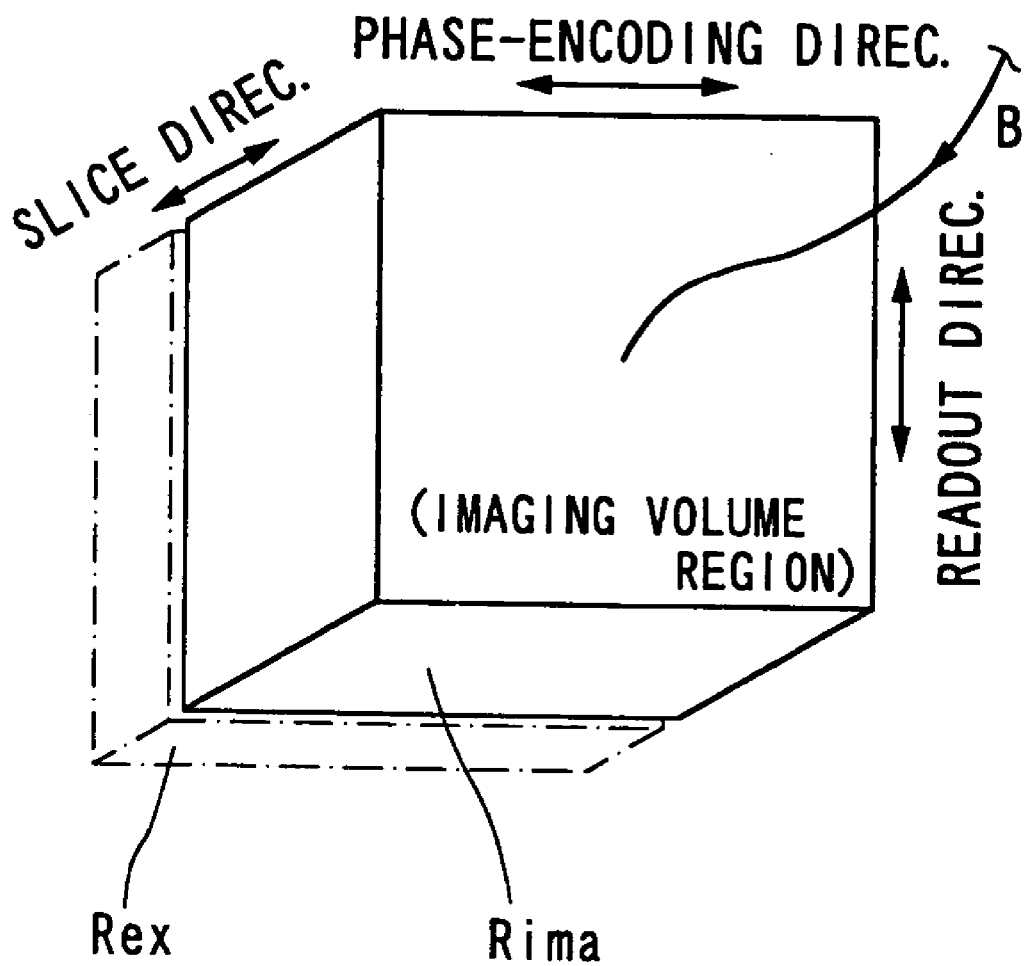
FIG. 20 illustrates an imaging region employed in the third embodiment.

Referring to FIGS. 18 to 20, a third embodiment of the present invention will be described.

The hardware construction of an MRI system of this embodiment is similar to those described in the foregoing embodiments.

The basic feature of the MRI system according to this embodiment is to use pulse sequences based on a single-shot (RF excitation) fast SE (spin echo) method on three-dimensional or two-dimensional slab (thick slice) scanning under ECG gating, in which MT (magnetization transfer) pulses of which flip angles and of which number are changeable are applied. The MT pulses are applied to give images MT contrasts based on MT effects fitted to imaging objects, and functions as means for produce an effective contrast between tissue and blood. Such pulse sequences are most effective in depicting the cardiac blood vessel systems. For instance, abdomen organs such as the heart can be imaged to provide T2-weighted contrast images. These images provides a tissue contrast between the cardiac muscle and the blood as high as that obtained by the conventional FE-system pulse sequences as well as a higher spatial resolution.

To realize such imaging, in the MRI system of this embodiment, the host computer 6 and the sequencer 5, shown in FIGS. 18 and 19, operates together to perform a scan on a pulse sequence preferred to imaging the cardiac blood systems. This pulse sequence is composed of a pre-sequence $SQ_{pre}$ performed first and an imaging data acquisition sequence $SQ_{acq}$ that follows the pre-sequence. The pulse sequence is executed with computer control by the sequencer 5 instructed from the host computer 6 that is responsible for a predetermined main program not shown. MR signals acquired with this scanning are processed under a predetermined reconstruction routine by the arithmetic operation unit 10. Moreover, a MIP (maximum intensity projection) image for showing the blood vessel systems can be formed by the arithmetic operation unit 10.

The sequencer 5, which has a CPU and memories, stores pulse-sequence information sent from the host computer 6, and controls a series of operations to be performed by the gradient power supply 4, transmitter 8T, and receiver 8R according to the stored information.

What is referred to pulse-sequence information is all information required for operating the gradient power supply 4, transmitter 8T, and receiver 8R according to a pulse sequence.

For example, pulse-sequence information includes information concerning the strength of a pulsating current to be applied to the x-, y-, and z-coils 3x to 3z, and the application time and timing thereof. Additionally the sequencer 5 receives the digital echo data from the receiver 8R and transfer them to the arithmetic operation unit 10.

As for the data acquisition sequence $SQ_{acq}$ (shown in FIGS. 18 and 19) forming part of the pulse sequence, a two-dimensional (2D) slab scan or a three-dimensional (3D) scan into which a Fourier transform method is incorporated can be adopted, for example. Available fundamental pulse trains are SE-system pulse trains in which one time of spin excitation can produce a plurality of echo signals. Such pulse trains include various ones, such as a fast SE method (2D or 3D), an FASE (fast asymmetric spin echo) (2D or 3D) combining a fast SE method with a half-Fourier technique by which data acquisition for one slice or one slice encode is carried out for one time or a plurality of times of RF excitation (shot), an EPI (echo planar imaging) method categorized into the SE system, or a hybrid EPI method.

The arithmetic operation unit 10 receives digital echo data sent from the receiver 8R via the sequencer 5, maps the data in a Fourier space (or the k-space or frequency space) formed in an incorporated memory, and performs a two-dimensional or three-dimensional Fourier transform with the mapped data so as to reconstruct an image in the real space. Moreover, the arithmetic operation unit 10 carries out mutual synthesis of reconstructed image data. The Fourier transform may be performed by the host computer 6, not by the sequencer 5.

A preferred example of synthesis is addition in which reconstructed image data items of a plurality of frames are added up pixel by pixel or maximum intensity projection (MIP) in which a maximum pixel value is selected pixel by pixel from among reconstructed image data items of a plurality of frames. Addition includes simple addition, averaging, and weighting and addition.

The voice generator. 16, which consists of a, constituent of the breath hold instructing components, utters, for example, a voice message informing a patient of the start or end of a breath hold in response to a command sent from the host computer 10. In place of this voice generator, provided is a light generator instructing a patient of timing of breath hold with light on/off signals. Alternatively or in parallel with this voice massage, this embodiment uses another technique to inform the breath hold; that is, it is a method to use sounds generated by a gantry when gradient pulses are applied in a controlled manner.

A pulse sequence performed in this embodiment will be described with reference to FIGS. 18 and 19.

As shown in FIG. 18, the pulse sequence consists of a pulse train with an ECG-gating technique by which a data acquisition sequence is started with a delay of a predetermined time from a triggering signal in synchronism with R-waves of an ECG signal. The data acquisition sequence serves as a main scan for acquiring MR signals. Practically, the pulse sequence includes a pre-sequence $SQ_{pre}$ executed prior to the main scan and a data acquisition sequence $SQ_{acq}$ (main scan) that follows the pre-sequence. The delay time is set so that the data acquisition sequence $SQ_{acq}$ is carried out for an optimum period within one heart beat.

The pre-sequence $SQ_{pre}$ includes an MT pulse train $PT_{mt}$ that causes MT effects, a CHESS (chemical shift selective)

pulse P$_{chess}$ that suppresses the acquisition of MR signals emanated from fat (called fat suppression), gradient spoiler pulses SP$_s$, SP$_r$, and SP$_e$ for dephasing spins.

The MT pulse train PT$_{mt}$, which is shown in detail in FIG. 19, has a plurality of divided MT pulses MT$_1$ to MT$_n$ and a plurality of slice gradient pulses G$_s$ each applied in parallel with the pulses MT$_1$ to MT$_n$. Pluralities of MT pulses MT$_1$ to MT$_n$, which compose a train of multiple MT pulses, are continuously applied with no gap therebetween. A minute standby time Δt may be set between two MT pulses.

Each slice gradient pulse G$_s$ is turned on/off with a gapless state to the next one, concurrently with the MT pulses MT$_1$ to MT$_n$. As an alternative construction, pluralities of slice gradient pulses G$_s$ may be added in the form of a continuous one pulse. The polarity of this slice gradient pulse G$_s$ is set, as one example, such that, as shown in FIG. 20, an excitation region R$_{ex}$ opposite to a flow of blood B to be imaged inflowing into an imaging volume region R$_{ima}$ is excited with off-resonance. This off-resonance excitation is done to expect the inflow of fresh blood flow B, without previously being excited, into an imaging volume region R$_{ima}$.

Each MT pulse is an excitation RF pulse formed, for instance, by modulating with a sinc function an RF signal of a desired frequency offset value. The number of MT pulses are plural (for example, ten). Thus the MT pulses compose a plurality of divided MT pulses described before. The number of MT pulses, the value of a flip angle, and the number of an off-resonance frequency is properly altered by auto calculation with computers or manual calculation.

After n-sets of the MT pulse and the slice gradient pulse are applied in turn, the CHESS pulse P$_{chess}$ for fat suppression is applied. The CHESS pulse P$_{chess}$ is an RF pulse formed by modulating a desired RF signal with a sinc function whose τ-length corresponds to the chemical sifts between the proton spins of water and fat.

Following the application of the CHESS pulse P$_{chess}$, the spin-dephasing gradient spoiler pulses SP$_s$, SP$_p$, and SP$_r$ are applied only one time at a time in the slice, phase-encoding, and readout directions.

An objective to be imaged in this embodiment is a blood vessel system of the chest. In order to image this blood vessel system, it is necessary that both an ECG-gating technique and a T2-weighting imaging technique that requires the repetition time TR to be more than 1000 msec be used together and the ECG gating be performed over at least two heart beats. Thus, to prevent the imaging from being longer to increase an efficiency of imaging, the data acquisition sequence SQ$_{acq}$ is composed of a single-shot FSE method employing a half-Fourier technique on the basis of a three-dimensional or two-dimensional slab scan. The two-dimensional slab scan is a scan performed both in a slice thickness of about 30 to 60 mm and in a state that the number of multislices is 1 to 3 (that is, the number of slices is a few and MT effects occurring in them are equivalent to one slice).

Additionally, in the single-shot FSE method, an interval between mutually adjoining refocusing RF pulses, i.e., an ETS (echo train spacing) between mutually adjoining echo signals is shortened to about 5 msec.

The operation of this embodiment will now be described.

When the MRI system is activated, the host computer 6 and the sequencer 5 perform the pulse sequence shown in FIG. 18. The application of pulses according to this sequence is carried out via the x-, y-, and z-coils 3x to 3z and the RF coil 7 under the control of the sequencer 5.

The host computer 5 and sequencer 6 monitor the input of a triggering pulse from the ECG signal. In response to the triggering pulse which has been inputted, the sequencer 5 waits for an appropriately predetermined delay time T$_D$ (for example, 300 to 500 msec) enabling the data acquisition sequence SQ$_{acq}$ to be delayed properly. The delay time T$_D$ is set to a proper value in advance so that imaging is allowed in an optimum range of one heart beat, where flow of blood outputted from the heart is stable in a mesodiastole.

On completing the above weighting period, the sequencer 5 orders the performance of the pulse sequence shown in FIGS. 18 and 19. Concurrently with this, the host computer 6 informs a patient of her or his breath hold via the voice generator 14 in response to the triggering pulse in a manner such that the breath hold fully covers the execution period of the pulse sequence.

When the pulse sequence is initiated, first, a plurality of divided MT pulses MT$_1$ to MT$_n$ composing the MT pulse train PT$_{mt}$ and the slice gradient pulses G$_S$ each having a predetermined strength and polarity are applied to an excitation region R$_{ex}$ in sequence in a slice selective mode. Each MT pulse has a frequency band that offsets by a predetermined value against a region R$_{ima}$ to be imaged. In consequence, the divided plural MT pulses give off-resonance excitation to the imaging volume region R$_{ima}$. Thus, the spins of the parenchyma and blood existing in the imaging volume region R$_{ima}$ are subject to gradually divided MT effects.

As mentioned before, these MT effects function as the sum of each MT pulse for the stationary parenchyma of the imaging volume region R$_{ima}$, the entire MT effects being almost equal to a state where a single MT pulse having a large flip angle (for example, 1000 degrees) is applied. Namely the MT effects are large, and echo signals later acquired show a substantial decrease in intensity. On the contrary, blood flowing through the imaging volume region R$_{ima}$ receives largely weakened MT effects as a whole, because of the divided MT pulses.

Echo signals from such blood, therefore, do not decrease so much in intensity. Additionally, as shown in FIG. 20, a blood B inflowing into the opposite side of the imaging volume region R$_{ima}$ to the excitation region R$_{ex}$ is still fresh, because. MT effects are scarcely given them.

After the application of the MT pulse train PT$_{mt}$, the sequencer 5 instructs necessary components to apply the CHESS pulse P$_{chess}$. In response to this, the CHESS pulse is applied to a region containing the imaging volume region R$_{ima}$ for fat suppression. Only the protons of fat resonate with the CHESS pulse, resulting in previous saturation of spins.

In succession, the gradient spoiler pulses SP$_s$, SP$_r$, and SP$_e$ are applied as end spoilers in the slice, readout, and phase-encoding directions. Thus, spins still left in the lateral magnetization are sufficiently dephased in each direction and saturated by the spoilers SP$_s$, SP$_r$, and SP$_e$. By this application, signals from the fat protons become zero effectively, excluding interference of spin phases with the data acquisition sequence, and preventing occurrence of pseudo echoes.

The spoiler pulse may be applied in only any one or two directions.

At a time when the pre-sequence SQ$_{pre}$ ends, the above-said delay time T$_D$ is to elapse. The sequencer 5 immediately starts performing the data acquisition sequence SQ$_{acq}$. As stated before, this sequence SQ$_{acq}$ is performed based on a 3D single-shot FSE with a half-Fourier technique. With this FSE sequence, under each amount G$_{E2}$ of slice encoding obtained by altering the slice gradient G$_s$, a plurality of echo signals responding to a plurality of refocusing RF pulses are acquired. Namely, echo signals that correspond to one slice-encoding amount are acquired by one shot.

The "3D single shot" referred herein is used to mean both (i) all data necessary for reconstructing a 3D image are acquired at one time of excitation and (ii) all data corresponding to one slice-encoding amount are acquired by one time of excitation (however, since the half-Fourier technique is adopted in this embodiment, "all data" do not mean all phase-encoded data corresponding to one slice-encoding amount.).

Echo signals for one slice-encoding amount are sequentially sent to the receiver 8R via the RF coil 7. The echo signals are processed into digital data by the receiver 8R, then stored into the arithmetic operation unit 10.

The acquisition of all the echo data that correspond to one slice-encoding amount is completed within a period of about 300 to 500 msec. It is preferred that the pulse sequence for one slice encode be completed within a one heart beat, as illustrated in FIG. 18.

After the first scanning, the sequencer 5 waits for a plurality of heartbeats without performing any scan For example, this waiting lasts until the triggering pulse associated with the third heartbeat is inputted. When such triggering pulse is received, the sequencer 5 performs the same pulse sequencer as that described above and the host computer 6 concurrently commands the breath hold. As a result, the repetition time TR is kept to, for example, a period of 3R-R, which normally takes appro. 3000 msec. It is therefore possible to provide T2-weighting images.

By performing the ECG-gating imaging a plurality of times responsively to the R-waves appearing, for example, every 3R-R, three-dimensional image data are acquired from the imaging volume region $R_{ima}$. The acquired data are then mapped in a three-dimensional Fourier space set in memories incorporated in the unit 10. On completing the data acquisition, the arithmetic operation unit 10 receives a command for image reconstruction from the host computer 6. Responsively to this command, the unit 10 performs a three-dimensional Fourier transform to reconstruct the mapped echo data into image data in the real space. In addition, the arithmetic operation unit 10 performs MIP processing with the reconstructed three-dimensional image data so as to produce a two-dimensional MR image. These three-dimensional and two-dimensional data may be stored into the storage unit 11 and presented on the display unit 12.

MR images of, for example, the blood system in the chest obtained by the MRI system of the present embodiment have a wide variety of advantages and features as below.

(1) Firstly, the pulse sequence based on the FSE method with the half-Fourier technique (i.e., FASE method) is performed with the ECG-gating technique and the repetition time TR of more than 1000 msec is secured. In consequence, T2-weighted contrast images of clinically significant is surely obtained.

(2) In obtaining such T2-weighted images, scanning is done at one shot. Therefore, although it is assured that the repetition time TR has a sufficient interval, an imaging time can be avoided from being longer.

(3) In this embodiment, since the data acquisition for T2-weighted images is done in relatively longer intervals of ECG gating, a period for the data acquisition sequence in the repetition time TR is shortened significantly. Because of this, an intermittent breath hold can be informed with adequate control means. Using both the ECG-gating and breath-holding techniques together can avoid artifacts owing to the respiratory move of the heart from occurring in a steady fashion.

(4) Further, in addition to one shot imaging in the 3D scan for one slice-encoding amount, the echo train spacing (ETS) is shortened and the excitation slab is thickened. This manner can not only suppress an increase in blood signal but also reduce motion artifacts.

(5) Furthermore, the MT pulse is used as a plurality of divided MT pulses. Therefore, as stated before, a contrast between stationary parenchyma and flowing or tumbling blood can be provided highly.

(6) Because the 3D scan (including the 2D scan of the less number of slices or single slice) is adopted, it is not required to perform multislice imaging. Hence the number of times of RF excitation can be reduced, avoiding a noticeable decrease in signal intensity, which inherently occurs due to MT effects when the cardiac muscle tissue, the liver parenchyma, or others are multislice-imaged with the FSE method. It is known that MT effects are effective in depicting flow of blood by improving a tissue contrast of the heart. In this embodiment, as a plurality of divided MT pulses are gradually applied, the total amount of MT effects can be controlled, thus providing an appropriate and effective tissue contrast.

(7) Where pulse sequences according to the FE system are used, shortening the entire data acquisition time necessitates the repetition time TR to be shortened. In order to meet such demand, a segmented technique based on the ECG gating is carried out every gate. In contrast, a T2-weighted imaging in compliance with the FSE method of the present embodiment permits the repetition time TR to be longer, without an extreme prolonged scan time. Thus, a standby time (for example, 300 to 600 msec) from the triggering pulse responding to an R-wave to the diastole suitable for heart imaging can effectively be used to instruct the breath hold and apply the MT pulses and CHESS pulse. It is clear that there is no temporal limitation on performing the pre-sequence $SQ_{pre}$. This eliminates the need for increasing a maximum of SAR (RF exposure) or maximum amplitudes of RF pulses. The number of MT pulses, their flip angles, and others can be set independently on each other to improve an image contrast with a high degree of freedom in setting the factors. A desired amount of MT effects is obtained at a minimum SAR value.

(8) The gradient spoiler pulses are applied only one time at the last of a train of pulses including the MT pulse train and CHESS pulse, which is able to shorten the entire pre-sequence time. So, a plurality of divided MT pulses each having a shortened duration is capable of generating steady MT effects.

(9) In applying the MT pulses, the polarities of the slice gradient pulses are controlled to excite in an off-resonance manner the opposite side of an excitation region $R_{ex}$ to inflowing blood. Thus, the spins within the imaging volume region $R_{ima}$ are not excited by the MT pulses, but undergo only MT effects. Desired flow of blood inflows into the imaging volume region $R_{ima}$ in a state that their spins have not been excited yet.

As a result, signal intensities from the blood flow become high and a contrast between parenchyma and blood flow is improved.

(10) Moreover, intervals between the refocus RF pulses are shortened, which prevents the drops of signals from blood or the occurrence of motion artifacts which were problems against the conventional FSE method. In association with such shortened intervals, there are other advantages;

a) the windows for data acquisition can be shortened, leading to a reduced influence on the motions of organs or the body, which reduces the occurrence of artifacts, b) an amount of blood outflowing for an interval between adjoining refocus RF pulses can be lowered, increasing signal intensities from blood, c) blurring of images resulting from T2 relaxation can be improved, improving an image resolution, and d) changes in the echo time TE in the central region in the phase-encoding of the k-space can be kept low, providing an excellent degree of image contrast equivalent or near to a degree of image contrast obtained by the SE scan of which echo time TE is the same.

(11) Still, the MRI system of this embodiment is able to provide an optimum echo train spacing ETS in the three-dimensional scan. In the two-dimensional scan, a fact that shortened intervals between the adjoining refocus RF pulses raise a depiction performance of blood systems has been known. However, findings through experiment and others conducted by the inventors show that simply applying into the three-dimensional scan the echo train spacing which has been used in the two-dimensional scan hardly depicts blood systems. It was also found that in the three-dimensional imaging, the length of the echo train spacing is very sensitive in depicting the blood systems of the chest.

In particular, even if an echo time spacing (ETS) of 10 to 15 msec which has been used by the conventional FSE scan is applied to imaging the heart, blurring of an image was large due to the motions. Shortening the ETS down to appro. 8 msec enabled imaging of the chest endurable to use. Specifically, a shortened ETS of about 5 msec showed a superior stabilization of images. A possible reason is considered such that, in addition to the foregoing various types of explanation, the shortened ETS makes it possible to put the entire data acquisition period within a cardiac stationary range of a heart beat.

On one hand, making the ETS long will lead to a long data acquisition window, which is possible to acquire data in a narrow band. That is, the ETS can be adjusted depending on the type of object to be imaged. For example, if a region to be imaged is distant from the chest, MR images of higher diagnostic capabilities can be obtained by setting an ETS of about 10 to 15 msec or more.

(12) In addition, in the case that the size of a matrix is increased in the phase-encoding direction, data acquisition based on the half-Fourier technique makes it possible to start imaging from the center or about in the k-space concerning a desired delay time $T_D$.

This reduces blurring of an image to a minimum.

(13) In multislice imaging, it is avoidable to have a saturation phenomenon of signals, which is caused by excitation pulses, from flow of blood in an adjoining slice.

(14) Furthermore, the delay time $T_D$ for the ECG-gating technique can be altered or controlled arbitrarily, producing MR images precisely reflecting the alteration or control. An appropriate delay time $T_D$ may be set depending on differences in individual patients in terms of magnetic characteristics.

(15) Because MR contrast mediums are not used, the feature of non-invasiveness is also obtained. Thus, compared with the contrast-based MRA imaging, the patient's mental and physical burdens are extremely reduced.

In this embodiment, the application step of the CHESS pulse may be omitted to compose the pre-sequence with a plurality of divided MT pulses alone.

Moreover, the MT pulse train can be set without the slice gradient pulse applied concurrently therewith. That is, the MT pulses are applied in a slice-non-selective manner. Also, the CHESS pulse for fat suppression can be applied slice-selectively with a slice gradient pulse applied concurrently with the CHESS pulse.

The MT pulses of the MT pulse train or the RF pulse of the CHESS pulse may be applied with a slice gradient taking account of a range to be imaged.

The command to control the breath hold period can be realized by on/off-controlled light signals instead of using sound or voice.

The delay time for optimizing the temporal location of the data acquisition sequence $SQ_{acq}$ may be determined by specifying a time from an R-wave to the front of the pre-sequence $SQ_{pre}$.

Fourth Embodiment

Figure 21:
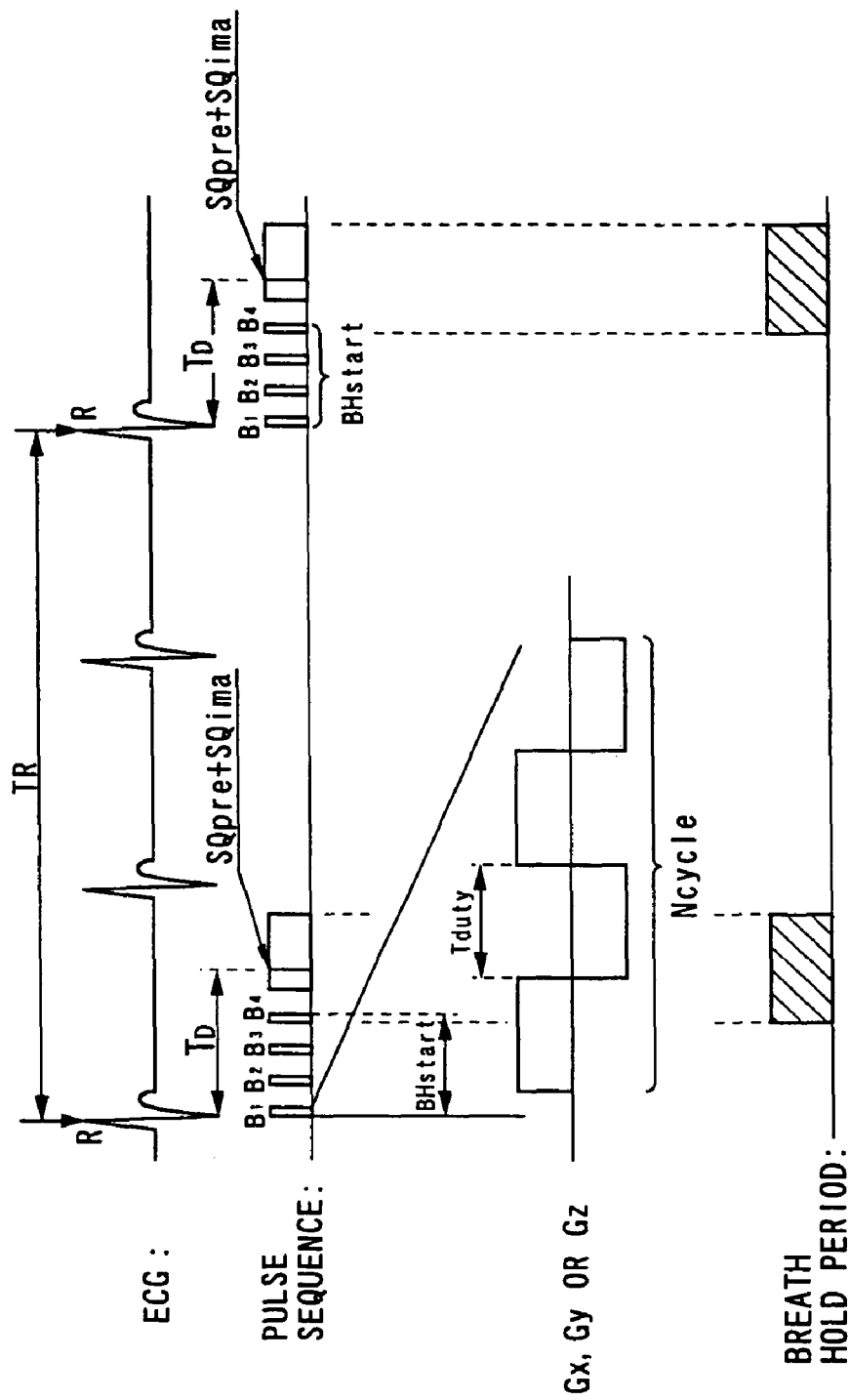
FIG. 21 is an outlined pulse sequence according to a fourth embodiment of the present invention.

Referring to FIG. 21, a fourth embodiment of the present invention will be described. An MRI system of this embodiment features a novel technique for informing patients of timing of her or his breath hold.

In ECG-gating imaging, one particular problem is that patient's respiratory body motions, which are in asynchronism with the ECG signal, deteriorates image quality. In the case of the conventionally known "segmented FFE scan," images are improved by using another means to detect such body motions. However, this embodiment employs a breath hold technique, not such body-motion-detecting means, in order to suppress influence caused by the respiratory body motions.

In the present invention, to obtain T2-weighted image contrast premises the elongation of the repetition time TR to 2000 msec or more. Therefore, the TR is set to a longer period of 4000 to 10000 msec, and the ECG gating is set to operate every four or about to ten heart beats or about. The breath hold is ordered every time the ECG gating operates, which gives an intermittent breath hold.

For the intermittent breath hold, how to inform patients of the start of each breath hold and its period are essential. Namely, significant matters are how precisely the start timing is given patients and to minimize the period of each breath hold. As one example of a minimized period of one breath hold, a period of data acquisition for each single shot scan is given as appro. 480 msec (=80+5×80) where the echo train spacing ETS=5 msec, echo time TE(effective TE)=80 msec, and the matrix size in the phase-encoding direction=160.

The fact that a standby period (the foregoing delay time) from a triggering pulse synchronous with an R-wave of the ECG signal to the diastole appropriate for imaging heart is relatively long; 300 to 600 msec, is positively used in the present embodiment. During the period, an intermittent breath hold that makes use of sound signals generated in association with applying gradient pulses is ordered, in addition to the application of the foregoing MT pulses and the CHESS pulse.

The host computer 6 and the sequencer 5 in this embodiment perform a pulse sequence including a sequence for intermittent breath holds shown in FIG. 21. As shown therein, in response to a not-shown triggering pulse synchronized with an R-wave, the sequencer 5 starts to apply a pulse train $BH_{start}$ urging a patient to hold her or his breath in a standby period $T_D$. As one example, the pulse train $BH_{start}$ consists of four pulses $B_1$ to $B_4$. Each of the pulses $B_1$ to $B_4$ has a pulse waveform made by repeating N-cycles a rectangular pulse of a given duty ratio $T_{duty}$. These pulses $B_1$ to $B_4$ are applied in turn via the x-, y-, or z-coil as X-axis, Y-axis, or Z-axis directional gradient pulses $G_x$, $G_y$, or $G_z$.

The application of these gradient pulses causes stresses owing to pulsed electromagnetic forces in a gantry structure sustaining the x-, y- and z-coils $3x$ to $3z$. These forces generate sound. For example, a patient laid in the gantry can hear a series of four intermittent sounds, like buzzer's sounds of "boo, boo, boo, boo. " The amplitude of these sounds can be controlled by adjusting the strength of the gradient pulses, while the tune thereof can be controlled by adjusting the duty ratio $T_{duty}$.

Immediately after these breath hold requesting sounds, the pulse sequence $SQ_{pre}$ and $SQ_{ima}$ formed in the same way as in the third embodiment is performed for one heart beat.

The patient is asked, in advance, as a promise, for performance of an intermittent breath hold in a manner such that; when you hear the intermittent sounds start, hold your breath for about one second or so (namely, a little time), after this, you can breaths. In particular, the 3D imaging requires timing of the breath hold not to be shifted. Therefore, it is preferred that the patient exercise the breath hold using the intermittent breath hold sequence shown in FIG. 21, prior to the actual imaging.

Accordingly, the patient can start holding her or his breath in the course of the intermittent breath-hold-requesting sounds and keep the breath-held state for a moment. A patient who is good at holding breath can start to hold her or his breath when the first sound is generated or the former several sounds are generated. Almost all patients can start to hold her or his breath at any time in a period during which all the intermittent sounds have continued. And the breath hold is done for a while, during which breath-held period the pre-sequence $SQ_{pre}$ and data acquisition sequence $SQ_{ima}$ are automatically and quickly performed. Under the performance of the pre-sequence $SQ_{pre}$ and data acquisition sequence $SQ_{ima}$, some kinds of sounds different from the breath-hold-requesting sounds are generated. Since the patient starts her or his breath hold in response to the intermittent sounds and keeps its hold state for a while, both the pre-sequence $SQ_{pre}$ and data acquisition sequence $SQ_{ima}$ are included in the breath hold state. When a few seconds have passed after having been released from the breath hold, another series of intermittent sounds are again generated, requesting the patient to perform the next breath hold.

Accordingly, the intermittent breath hold almost completely matched to the ECG gating time produced every a few heart beat can be done by patients. Because the breath hold is intermittent, even if the data acquisition period is longer to some extent, patients are able to hold her or his breath easily. Artifacts caused by respiratory body motions can be suppressed greatly.

This intermittent breath hold can easily be performed with the existing MRI system new hardware; it is not necessary to add particular hardware. Differently from sound messages (saying words) that inform a patient of timing of the breath hold by a control computer, there is no need for executing processing for synchronism with imaging pulse sequence, facilitating the software processing.

Thus, there is provided an MRI system by which the intermittent breath hold for a self navigator technique for the breath hold can be performed that is novel, prominent, and suitable for 3D ECG-gating imaging. Various advantages coming from the FSE scan are also obtained, like the third embodiment.

Fifth Embodiment

Figure 22:
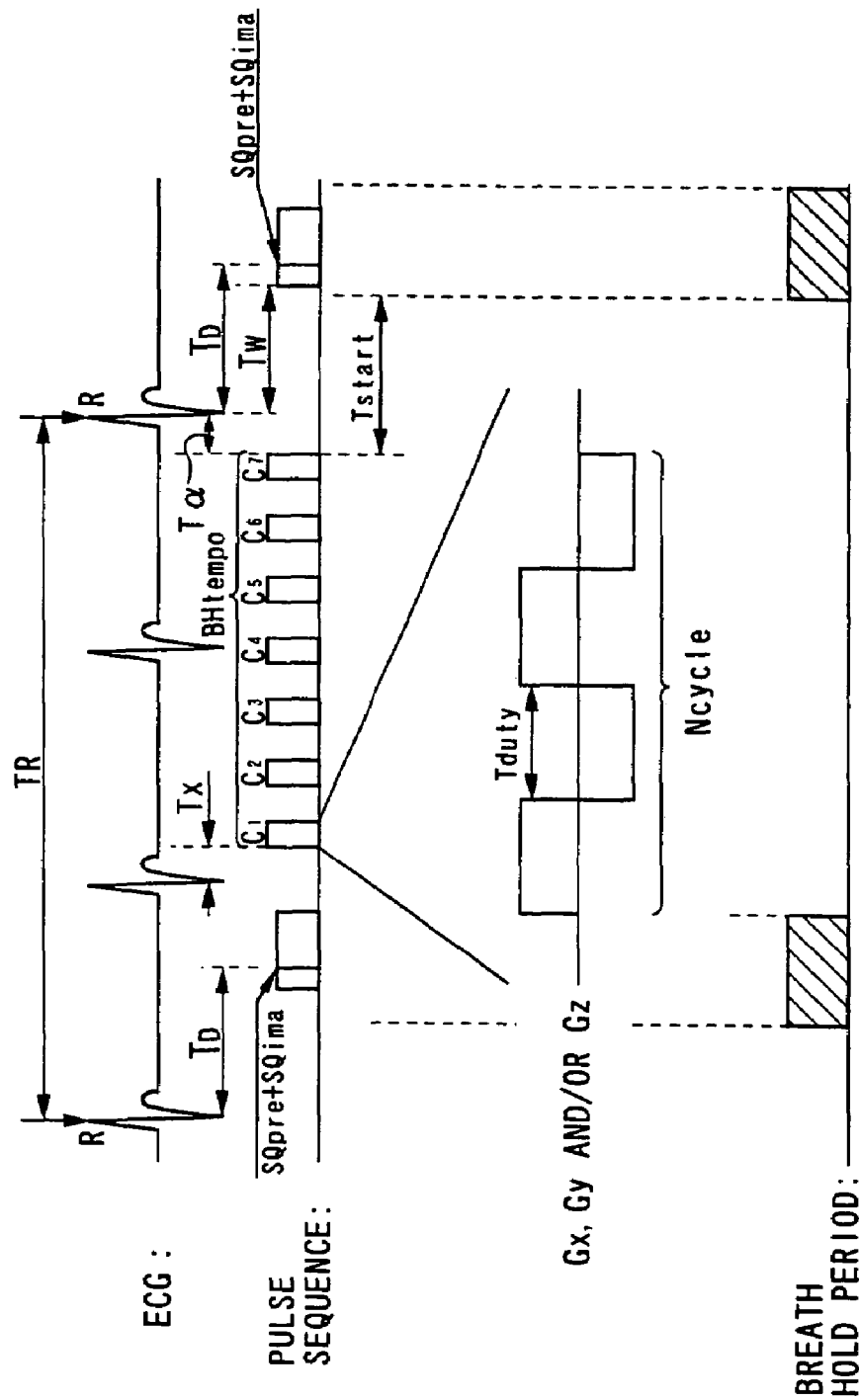
FIG. 22 is an outlined pulse sequence according to a fifth embodiment of the present invention.

Referring to FIG. 22, a fifth embodiment of the present invention will be described, which provides another configuration about the foregoing intermittent breath hold technique.

The host computer 6 and the sequencer 5 of this MRI system are constructed to perform a pulse sequence (including an intermittent breath-hold sequence) shown in FIG. 22. As shown therein, the sequencer 5 responds to a triggering pulse (not shown) synchronizing with an R-wave of the ECG signal. When a standby time $T_X$ has passed after this response, the sequencer 5 informs a patient of a period during which the patient can breathe freely (referred to as "free breath period) by applying a pulse train $BH_{tempo}$ for preparing for the breath hold. The pulse train $BH_{tempo}$ is made up of, for example, seven pulses $C_1$ to $C_7$, which are applied over a few heartbeats for a vacant period in one repetition time TR, no data acquisition being carried out in the vacant period.

Each of the pulses $C_1$ to $C_7$ has a pulse waveform made by repeating N-cycles a rectangular pulse of a given duty ratio $T_{duty}$. These pulses $C_1$ to $C_7$ are applied via the x-, y-, and/or z-coil as X-axis, Y-axis, and/or Z-axis directional gradient pulses $G_x$, $G_y$, or $G_z$.

Like the foregoing embodiment, the application of the gradient pulses permits the gantry to produce sounds. For example, a patient laid in the gantry can hear a series of seven intermittent sounds, like buzzer's sounds of "boo, boo, boo, . . . , boo", as breath-hold preparing sounds. The amplitude of these sounds can be controlled by adjusting the strength of the gradient pulses, while the tune thereof can be controlled by adjusting the duty ratio $T_{duty}$.

After the generation of the breath-hold preparing sounds, a given standby period $T_{start}$ is set. This standby time is then followed by the same pulse sequences $SQ_{pre}$ and $SQ_{ima}$ as those in the third embodiment. The standby time $T_{start}$ is composed of a given waiting time $T_w$ counted from an R-wave assigned to imaging and a little margin $T_\alpha$.

A promise to the patient is that; when you hear the intermittent sounds stop, hold your breath for about two seconds or so (namely, a little time), after this, you can breaths. In this case, it is also preferred that the patient exercise the breath hold using the intermittent breath hold sequence shown in FIG. 22, prior to the actual imaging.

Thus, the patient can be ready for a breath hold by adjusting her or his breath using the breath-hold preparing sounds (intermittent sounds). The breath hold can be done for about two seconds during after the preparing sounds. Therefore, most of the standby time $T_{start}$ and the pulse sequences $SQ_{pre}$ and $SQ_{ima}$ are completely included in a period of the breath hold. After this appropriate breath-hold period, the patient can breaths freely. In succession, every time the breath-hold preparing sounds are generated, the same breath hold is repeated.

Accordingly, the same or similar advantages as or to those in the fourth embodiment can be obtained.

There is also the advantage that the intermittent breath-hold technique is widened in variations. This technique can be selected depending on individuals. The breath hold is made sure in ECG-gating 3D imaging.

In the foregoing fourth and fifth embodiments, the intermittent breath hold is characteristic of being applied to a pulse sequence associating with a pre-sequence employing the MT pulse train and the CHESS pulse. Alternatively, the intermittent breath-hold technique is also applicable to other pulse sequences for 3D imaging.

Sixth Embodiment

Figure 23:
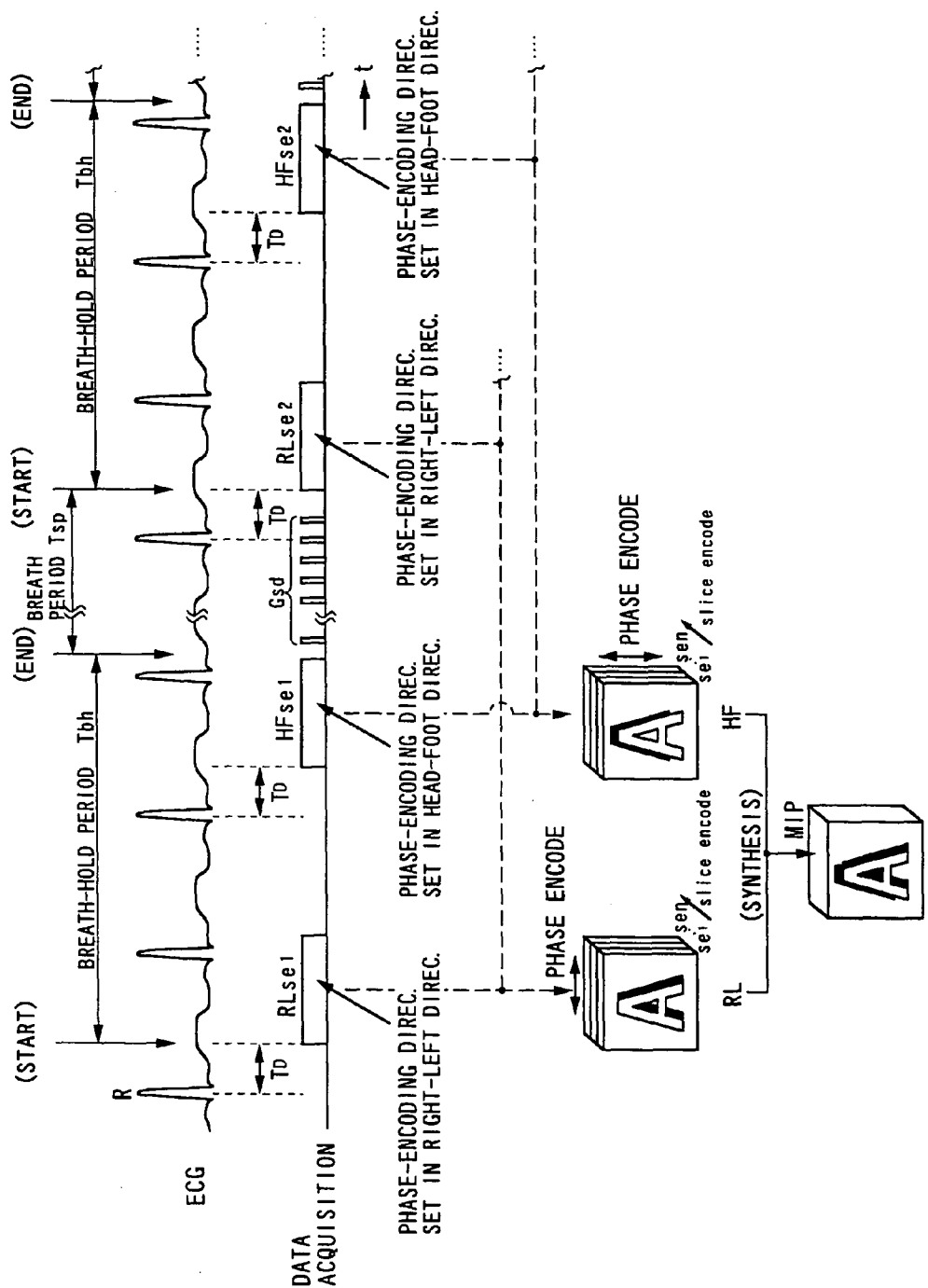
FIG. 23 is an outlined pulse sequence according to a sixth embodiment of the present invention.
Figures 24A, 24B:
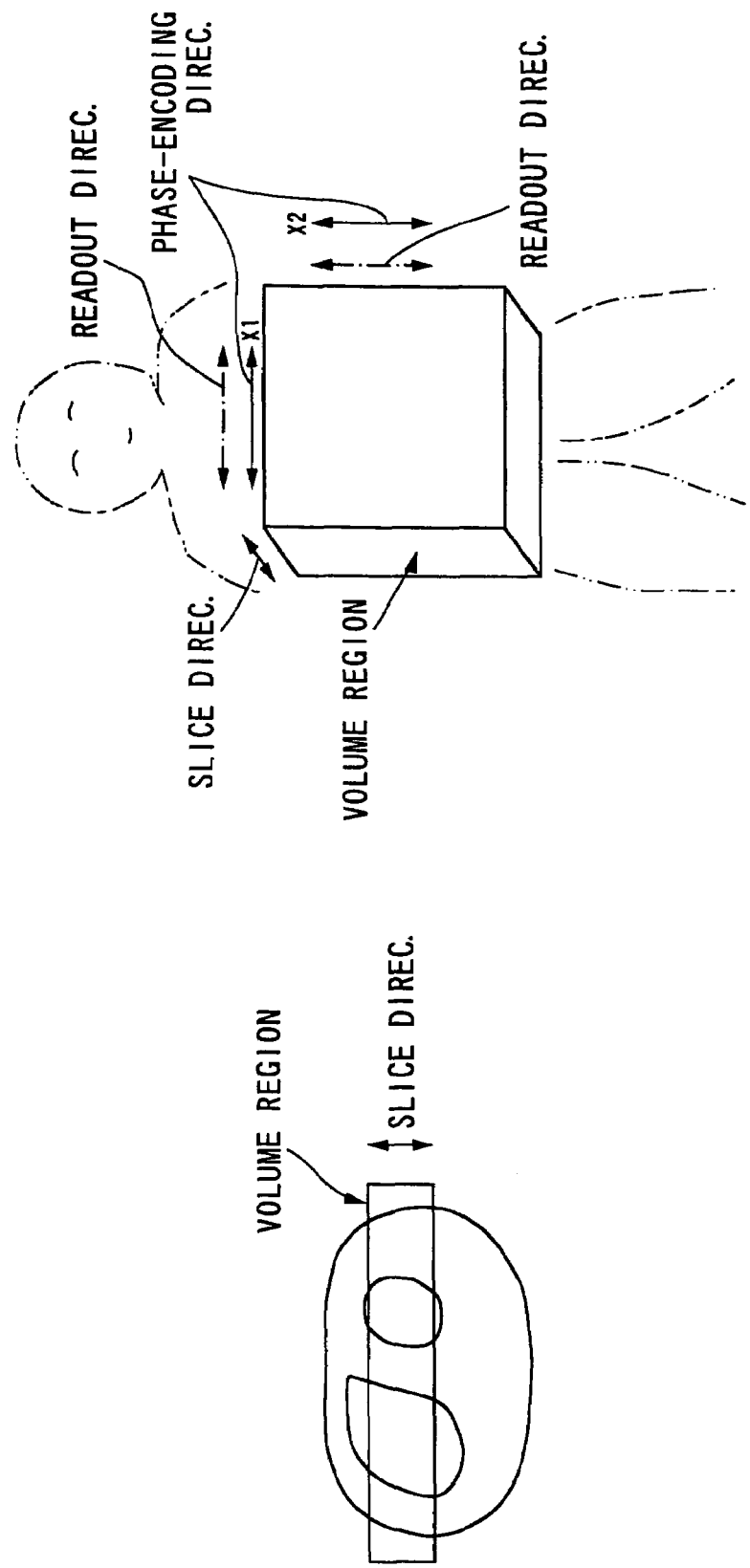
FIGS. 24A and 24B pictorially show a imaging region in the sixth embodiment.

Referring to FIGS. 23 and 24A, 24B, a sixth embodiment of the present invention will be described. This embodiment is concerned with one usage of the intermittent breath-hold technique described above.

More specifically, this intermittent breath-hold technique is adopted into a 3D SPEED (Swap Phase Encode Extended Data) method.

The SPEED method, as proposed by "JMRI, Miyazaki.m. et al., 98 March/April", is a 2D or3D imaging technique in which data acquisition is performed for one image with the phase-encoding direction altered. In case of 3D SPEED imaging, with the slice-encoding direction fixed, image data are acquired a plurality of times for different phase-encoding directions. At the stage of processing image data, three-dimensional raw data are reconstructed every phase-encoding direction, then a plurality of sets of resultant real-space three-dimensional image data are synthesized with each other, pixel by pixel, into one set of three-dimensional image data.

In this embodiment, pluralities of times of scans are performed with the phase-encoding and readout directions mutually swapped, but with the slice direction unchanged. FIG. 23 outlines a scan instructed by the host computer 6 and sequencer 5.

In addition to the SPEED method, this scanning adopts ECG-gating and intermittent breath-hold techniques. A delay time $T_D$ that determines an ECG-based synchronization time is set in advance so as to bring a period of data acquisition into an appropriate cardiac phase.

For example, as shown in FIGS. 24A and 24B, data acquisition from a three-dimensional volume region set in the abdomen is carried out with 2n-times (n is positive integer more than 1) of scans in the order of $RL_{se1}$, $HF_{se1}$, $RL_{se2}$, $HF_{se2}$, . . . , $RL_{sen}$, $HF_{sen}$, under the FASE method, for example. Each of the scans $RL_{se}$ and $HF_{se}$ represents an ECG-gating single scan for each slice-encoding amount, which provides three-dimensional raw data of the volume region. However, the phase-encoding direction differs between the scans $RL_{se}$ and $HF_{se}$. For the scan $RL_{se}$, the phase-encoding direction is set in the lateral direction of the patient's body, as shown by a solid line X1 in FIG. 24B. In contrast, for the scan $HF_{se}$, the phase-encoding direction is set in the longitudinal direction of the patient's body, as shown by a solid line X2 in FIG. 24B, which is different from the direction X1 by 90 degrees. The subscripts $se_1$, . . . , $se_n$ show amounts of slice-encoding for each scan. According to the exemplified sequence shown in FIG. 23, the first and second ECG-gating scans are each performed every slice-encoding amount $se_1$ (to $se_n$).

In imaging the chest and abdomen portion, the breath hold is absolutely necessary in order to prevent respiratory artifacts. However, because it takes a long time to perform a three-dimensional scan, it is difficult to cover the whole imaging time by one time of breath hold. The breath hold is therefore carried out intermittently. This intermittent breath hold is characteristic of informing a patient of timing distinguishing a breath-hold period $T_{bh}$ (i.e., data acquisition period) and a free breath period $T_{sp}$ with sounds caused by applying gradients.

In the case of FIG. 23, such distinguishing timing is determined such that one pair of the scans $RL_{se1}$ and $HF_{se1}$ is made and the breath-hold period $T_{bh}$ is assigned to a period during which one pair of scans last. The free breath period $T_{sp}$ is assigned to the following period lasting to the next data acquisition (for example, in the case of a period between the scans $HF_{se1}$ and $RL_{se2}$).

This free breath period $T_{sp}$ is informed of a patient by breath-hold preparing sounds generated by applying gradients. Like the foregoing embodiments, the preparing sounds are generated by applying a gradient pulse $G_{sd}$, . . . , $G_{sd}$ in the X-, Y-, and/or Z-axis directions. The breath-hold preparing sounds can be heard intermittently generated at intervals, like buzzer's sounds "boo, boo, . . . , boo."

The amplitudes and tones of the breath-hold sounds can be controlled appropriately by adjusting parameters concerning the gradient pulses $G_{sd}$. It is preferred that intervals of a patient's respiration (the pace of respiration) be examined in advance in her or his natural state, and each interval in the breath-hold preparing sounds (that is, the number of sounds produced during the free breath period $T_{sp}$) be made to agree with each respiration interval.

A single set of three-dimensional raw data whose phase-encoding direction is set laterally are reconstructed into a set of image data, while another single set of three-dimensional raw data whose phase-encoding direction is set longitudinally are also so. Both the three-dimensional image data thus-reconstructed are synthesized pixel by pixel into a new one set of three-dimensional image data. For each slice encode, two frames of data whose phase-encoding directions differ from each other undergo MIP processing, providing a final three-dimensional MRA data. The image synthesizing processing may be simple adding or averaging.

According to this embodiment, the ECG-gating timing (i.e., delay time $T_D$) is optimized beforehand, scanning can be performed so as to acquire echo signals having the highest intensities from flow of blood. It is firmly avoidable that echo signals are lowered or become almost zero on account of relatively slow velocities of flow of blood or occurrence of a flow-void phenomenon. The optimized synchronization timing produces MRA images of a stable and higher depiction performance. Use of FSE-system pulse sequences is advantageous in susceptibility and distortions of contours.

Moreover, final image data are produced from data acquired a plurality of times with altered phase-encoding directions. Because of altering the phase-encoding directions, the image data thus acquired are superior in the depiction performance, especially when flow of blood whose T2 relaxation time is shorter is imaged. This is because effects that pixel values are enhanced (or blurred) in the phase-encoding direction can be utilized. Pulmonary blood vessels that run in all directions are depicted with higher ratios of S/N and higher contrast degrees of parenchyma, providing finer bits of information about running directions of blood vessels.

Concerning the intermittent breath-hold technique informing patients of the breath-hold and free breath periods, following advantages can be obtained.

First, only the gradient pulses $G_{ds}$, . . . , $G_{ds}$ are added to the imaging pulse sequence, and there is no need for installing special hardware units. The processing for controlling sound generation is relatively easier.

It is easy to synthesize both the imaging pulse sequence and the ECG signal.

Secondly, the tones, magnitudes, and intervals of the breath-hold preparing sounds can be easily adjusted by parameters about the pulses $G_{ds}$, . . . , $G_{ds}$. Particularly, the intervals of the intermittent sounds can previously be set to the pace of a patient's natural respiration. In that case, it is easier to capture the start timing of the breath-hold period next to a free breath period. Namely, a patient can breathe in agreement with the breath-hold preparing sounds (intermittent sounds) in a free breath period, and starts a breath hold when the last one of the preparing sounds is heard. The number of preparing sounds will be taught to a patient in advance or the last sound will be differentiated in tone from the other ones. Thus, instructions for the breath hold are easy to be understood, resulting in that a patient can enter a steady breath-hold period.

The steady and stable breath hold allows artifacts caused by the respiratory motions to be reduced.

Even if automatic sound massages saying words are generated together with this intermittent sound technique, the intermittent breath hold can be easier, because the number of breath-hold preparing sounds define free breath periods.

The third advantage of this embodiment is that operator's work required for the breath hold is noticeably reduced thanks to this self navigator technique for the breath hold. The efficiency of operation and a patient throughput are improved.

Seventh Embodiment

Figure 25:
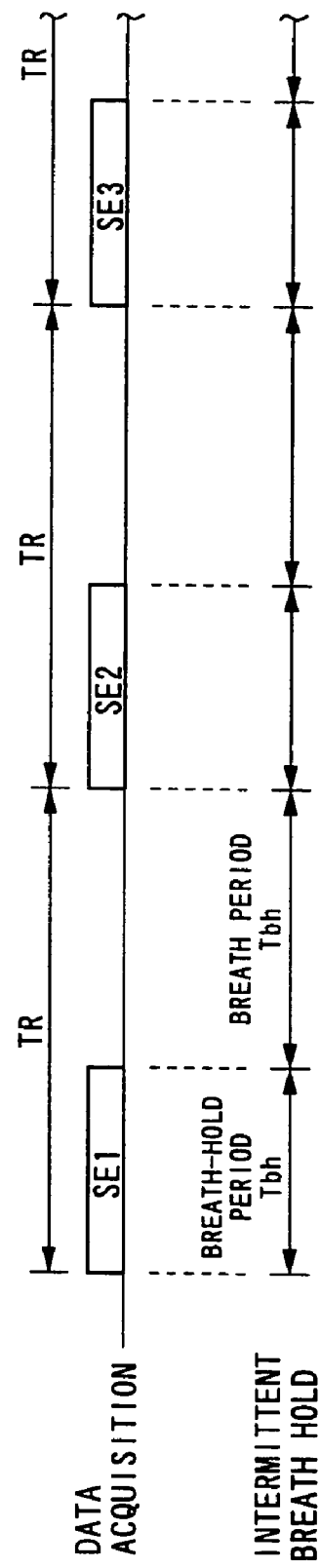
FIG. 25 is an outlined pulse sequence according to a seventh embodiment of the present invention.

Referring to FIG. 25, a seventh embodiment of the present invention will be explained. This invention also concerns another example of the intermittent breath hold.

This embodiment provides an imaging technique in which the intermittent breath hold is incorporated into such three-dimensional imaging as 3D-MRCP (MR cholangiopancreatography). In the 3D imaging, the intermittent breath hold is absolutely necessary, because of its long scan time. Particularly, to depict entities having longer T2 relaxation times needs the repetition time to be longer. Thus, it is difficult to complete the entire imaging within one time of breath hold.

Therefore, as shown in FIG. 25, a breath-hold period $T_{bh}$ and a free breath period $T_{sp}$ are repeated every time when the slice-encoding amount SE is altered. The free breath period $T_{sp}$ is assigned to the intermittently remaining intervals other than periods (breath-hold periods $T_{bh}$) when a pulse sequence for data acquisition is applied. A patient is informed of these intermittent periods $T_{sp}$ using breath-hold preparing sounds generated by applying gradient pulses $G_{sd}, \ldots, G_{sd}$. In this embodiment, the first breath-hold period $T_{bh}$ is set to a data acquisition period for the slice-encoding amount $SE_1$, and a remaining interval of the repetition time TR is the first free breath period $T_{sp}$. Like this, the periods are repeated.

Control of the breath-hold preparing sounds is done in the same way as in the sixth embodiment. The control is united with imaging control of the pulse sequence, and the host computer 6 and the sequencer 5 operates cooperatively to perform the imaging control.

Each set of 3D raw data acquired every slice-encoding amount with the foregoing intermittent breath hold are subject to a 3D Fourier-transform in the arithmetic operation unit 10, providing 3D real-space image data.

Therefore, the equivalent advantages to the sixth embodiment are obtained.

In the sixth and seventh embodiments, MR angiography was an object to be imaged, but it is not limited to only blood vessels. For example, a filamentous tissue may be another objective. In particular, if an objective has a longer T2 relaxation time, such objective can be imaged well.

Imaging methods to which the intermittent breath hold of the present invention is applied are not restricted to the ones mentioned above. For example, dynamic imaging can be done using such breath hold technique. The dynamic imaging often requires that several times of imaging be performed before and after injecting a contrast medium, respectively. In this case, it is preferred that a patient be informed of a period for the free breath (in other words, timing of starting breath holds) by the foregoing preparing sounds generated by applying the gradient pulses, as described above. Still, the intermittent breath hold of the invention can also be adopted to discontinuous imaging methods, such as segmented FFE (Fast FE) preferable to imaging of the heart.

Moreover, as means for detecting the cardiac temporal phases, the foregoing ECG-related elements may be replaced by any other means, such as gating means to uses pulses detected from a finger of a patient, gating means to use echo signals themselves, or others.

Though the present embodiments have been put into practice with respect to the blood of a patient object, these imaging techniques can also be used to image cerebral spinal fluid (CSF) or other fluid moving within the object.

Although the description above contains many specificities, these should not be construed as limiting the scope of the invention but as merely providing illustrations of some of the presently preferred embodiments of this invention. Thus the scope of this invention should be determined by the appended claims and their equivalents.

What is claimed is:

1. A magnetic resonance imaging (MRI) system providing an MR image of an imaging region of an object, said system comprising, an MT (magnetization transfer) pulse applying unit configured to apply an MT pulse to the object so as to cause an MT effect in the imaging region, the MT pulse consisting of a plurality of divided MT pulses applied sequentially in time, a flip angle of each divided MT pulse being 90 to 100 degrees, and a region to be excited by the MT pulse spatially including the imaging region;

a gradient spoiler pulse applying unit configured to apply a gradient spoiler pulse to the object after applying the MT pulse;

a scanning unit configured to scan the imaging region with a pulse sequence to acquire an MR signal from the imaging region after applying the gradient spoiler pulse; and an image producing unit configured to produce the MR image using the acquired MR signal.

2. The MRI system of claim 1, wherein each of the plurality of divided MT pulses applied by the MT pulse applying unit comprises an RF pulse of which frequency is set to a value exciting magnetic spins residing in the imaging region.

3. The MRI system of claim 2, wherein each of the plurality of divided MT pulses applied by the MT pulse applying unit is shorter in duration than a slice-selective MT pulse.

4. The MRI system of claim 3, wherein the duration of each divided MT pulse is as short as approximately 1300 μsec.

5. The MRI system of claim 1, wherein the gradient spoiler pulse applying unit is configured to apply to the object the gradient spoiler pulse in at least one of slice, readout and phase-encoding directions spatially set to the object, the slice, readout and phase-encoding directions being perpendicular to each other.

6. A magnetic resonance imaging method of providing an MR (magnetic resonance) image of an imaging region of an object, the method comprising the steps of:

applying an MT (magnetization transfer) pulse to the object so as to cause an MT effect in the imaging region, the MT pulse consisting of a plurality of divided MT pulses applied sequentially in time, a flip angle of each divided MT pulse being 90 to 100 degrees, and a region to be excited by the MT pulse spatially including the imaging region;

applying a gradient spoiler pulse to the object after applying the MT pulse;

scanning the imaging region with a pulse sequence to acquire an MR signal from the imaging region after applying the gradient spoiler pulse; and producing the MR image using the acquired MR signal.

7. The magnetic resonance imaging method of claim 6, wherein each of the plurality of divided MT pulses comprises an RF pulse of which frequency is set to a value exciting magnetic spins residing in the imaging region.

8. The magnetic resonance imaging method of claim 7, wherein each of the plurality of divided MT pulses is shorter in duration than a slice-selective MT pulse.

9. The magnetic resonance imaging method of claim 8, wherein the gradient spoiler pulse is applied in at least one of slice, readout and phase-encoding directions spatially set to the object, the slice, readout and phase-encoding directions being perpendicular to each other.

10. The magnetic resonance imaging method of claim 8, wherein the duration of each MT pulse divided is as short as approx. 1300 μsec.

11. A magnetic resonance imaging method comprising, in the following sequence:

applying at least one MT pulse to an object imaging region;

applying at least one gradient spoiler pulse to said object imaging region;

acquiring MR image data from said object imaging region; and producing an image using said acquired MR image data wherein said at least one MT pulse comprises a plurality of divided MT pulses, each having a duration shorter than the duration of a slice selective MT pulse.

12. A method as in claim 11 wherein said at least one MT pulse utilizes an RF frequency which MR excites magnetic spins in said object imaging region.

13. A method as in claim 11 wherein said at least one gradient spoiler pulse is applied in at least one of mutually perpendicular (a) slice, (b) readout and (c) phase-encoding directions.

14. A magnetic resonance imaging method comprising, in the following sequence:

applying at least one MT pulse to an object imaging region;

applying at least one gradient spoiler pulse to said object imaging region;

acquiring MR image data from said object imaging region; and producing an image using said acquired MR image data wherein said at least one MT pulse comprises a plurality of divided MT pulses, each having a duration no greater than approximately 1300 μsec.

15. A method as in claim 14 wherein said at least one MT pulse utilizes an RF frequency which MR excites magnetic spins in said object imaging region.

16. A method as in claim 14 wherein said at least one gradient spoiler pulse is applied in at least one of mutually perpendicular (a) slice, (b) readout and (c) phase-encoding directions.

* * * * *